(12) United States Patent
Soller

(10) Patent No.: US 8,818,477 B2
(45) Date of Patent: Aug. 26, 2014

(54) PHYSICAL PERFORMANCE MONITORING AND MONITORS

(75) Inventor: Babs R. Soller, Northboro, MA (US)

(73) Assignee: University of Massachusetts, Boston, MA (US)

( * ) Notice: Subject to any disclaimer, the term of this patent is extended or adjusted under 35 U.S.C. 154(b) by 1369 days.

(21) Appl. No.: 12/172,942

(22) Filed: Jul. 14, 2008

(65) Prior Publication Data

US 2009/0024013 A1 Jan. 22, 2009

Related U.S. Application Data

(60) Provisional application No. 60/949,789, filed on Jul. 13, 2007.

(51) Int. Cl.
*A61B 5/05* (2006.01)

(52) U.S. Cl.
USPC ........... 600/361; 600/322; 600/323; 600/324; 600/348; 600/317

(58) Field of Classification Search
None
See application file for complete search history.

(56) References Cited

U.S. PATENT DOCUMENTS

| | | | | |
|---|---|---|---|---|
| 4,223,680 A | * | 9/1980 | Jobsis | 600/324 |
| 4,321,930 A | * | 3/1982 | Jobsis et al. | 600/344 |
| 4,380,240 A | * | 4/1983 | Jobsis et al. | 600/344 |
| 5,497,769 A | * | 3/1996 | Gratton et al. | 600/323 |
| 5,582,170 A | | 12/1996 | Soller | |
| 5,757,002 A | | 5/1998 | Yamasaki et al. | |
| 5,813,403 A | * | 9/1998 | Soller et al. | 600/310 |
| 6,006,119 A | | 12/1999 | Soller et al. | |
| 6,052,194 A | | 4/2000 | Nuyan | |
| 6,216,021 B1 | | 4/2001 | Franceschini et al. | |
| 6,304,767 B1 | | 10/2001 | Soller et al. | |
| 6,542,762 B1 | | 4/2003 | Alam et al. | |
| 6,564,088 B1 | | 5/2003 | Soller et al. | |
| 6,587,702 B1 | | 7/2003 | Ruchti et al. | |
| 6,766,188 B2 | * | 7/2004 | Soller | 600/477 |
| 6,817,979 B2 | * | 11/2004 | Nihtila | 600/300 |
| 6,898,451 B2 | * | 5/2005 | Wuori | 600/322 |

(Continued)

FOREIGN PATENT DOCUMENTS

JP 06-142087 5/1994
JP 09-038051 2/1997

(Continued)

OTHER PUBLICATIONS

Casaburi et al., "Reductions in exercise lactic acidosis and ventilation as a result of exercise training in patients with obstructive lung disease," American Review of Respiratory Disease 143: 9-18 (1991).

(Continued)

*Primary Examiner* — Melanie Tyson
*Assistant Examiner* — Todd J Scherbel
(74) *Attorney, Agent, or Firm* — Fish & Richardson P.C.

(57) ABSTRACT

Methods and systems are disclosed for determining an anaerobic threshold and/or an oxygen consumption rate in a human or animal subject. The methods include exposing a tissue of the subject to illumination radiation, collecting emitted radiation from the tissue, the emitted radiation including a portion of the illumination radiation reflected or transmitted from the tissue, processing the emitted radiation to form a spectrum of the tissue, and determining, based on the spectrum of the tissue, the anaerobic threshold and/or the oxygen consumption rate of the subject.

9 Claims, 10 Drawing Sheets

(56) References Cited

U.S. PATENT DOCUMENTS

| | | | |
|---|---|---|---|
| 7,245,373 B2 | 7/2007 | Soller et al. | |
| 7,532,919 B2 | 5/2009 | Soyemi et al. | |
| 7,616,303 B2 | 11/2009 | Yang et al. | |
| 7,865,223 B1* | 1/2011 | Bernreuter | 600/323 |
| 7,881,892 B2 | 2/2011 | Soyemi et al. | |
| 8,082,015 B2* | 12/2011 | Yodh et al. | 600/310 |
| 8,417,305 B2* | 4/2013 | Dixon | 600/323 |
| 2002/0161290 A1* | 10/2002 | Chance | 600/323 |
| 2003/0032064 A1 | 2/2003 | Soller et al. | |
| 2003/0088163 A1 | 5/2003 | Soller | |
| 2004/0002634 A1* | 1/2004 | Nihtila | 600/300 |
| 2004/0005717 A1 | 1/2004 | Soller | |
| 2005/0021110 A1 | 1/2005 | Maschke et al. | |
| 2006/0281983 A1 | 12/2006 | Al-Ali et al. | |
| 2007/0038041 A1 | 2/2007 | Yang et al. | |
| 2008/0097173 A1 | 4/2008 | Soyemi et al. | |
| 2009/0024013 A1 | 1/2009 | Soller | |
| 2010/0198027 A1* | 8/2010 | Dixon | 600/323 |
| 2011/0184683 A1* | 7/2011 | Soller et al. | 702/85 |
| 2011/0205535 A1* | 8/2011 | Soller et al. | 356/300 |
| 2012/0245439 A1* | 9/2012 | Andre et al. | 600/310 |

FOREIGN PATENT DOCUMENTS

| | | |
|---|---|---|
| JP | 09-126995 | 5/1998 |
| JP | 2001-509589 | 7/2001 |
| JP | 2006-116161 | 5/2006 |
| WO | WO 99/29056 | 6/1999 |
| WO | WO 99/39630 | 8/1999 |
| WO | WO 2007/070093 | 6/2007 |
| WO | WO 2010/053617 | 5/2010 |

OTHER PUBLICATIONS

Older et al., "Preoperative evaluation of cardiac failure and ischemia in elderly patients by cardiopulmonary exercise testing," Chest 104: 701-704 (1993).
Hamaoka et al., "Noninvasive measures of oxidative metabolism on working human muscles by near-infrared spectroscopy," J. Appl. Physiol. 81: 1410-1417 (1996).
Older et al., "Cardiopulmonary exercise testing testing as a screening test for perioperative management of major surgery in the elderly," Chest 116: 355-362 (1999).
Gitt et al., "Exercise anaerobic threshold and ventilatory efficiency identify heart failure patients for high risk of early death," Circulation 106: 3079-3084 (2002).
Yang et al., "Simultaneous correction of the influence of skin color and fat on tissue spectroscopy by use of a two-distance fiber-optic probe and orthogonalization technique," Opt. Lett. 30: 2269-2271 (2005).
Whipp, "Physiological mechanisms dissociating pulmonary $CO_2$ and $O_2$ exchange dynamics during exercise in humans," Experimental Physiology 92: 347-355 (2007).
Search report and written opinion for international application PCT/US08/69998, dated Mar. 10, 2009, by searcher Lee W. Young.
Arbabi et al., "Near-infrared spectroscopy: A potential method for continuous, transcutaneous monitoring for compartmental syndrome in critically injured patients," J. Trauma 47: 829-833 (1999).
Beaver et al., "A new method for detecting anaerobic threshold by gas exchange," J. Appl. Physiol. 60: 2020-2027 (1986).
Belardinelli et al., "Changes in skeletal muscle oxygenation during incremental exercise measured with near infrared spectroscopy," European J. Appl. Physiol. Occupational Physiol. 70(6): 487-492 (1995).
Bhambhani et al., "Detection of ventilatory threshold using near infrared spectroscopy in men and women," Med. Sci. Sports Exerc. 29: 402-409 (1997).
Boushel et al., "Near-infrared spectroscopy for monitoring muscle oxygenation," Acta Physiologica Scandinavica 168: 615-622 (2000).
Caiozzo et al., "A comparison of gas exchange indices used to detect the anaerobic threshold," J. Appl. Physiol. Resp. Env. & Ex. Physiol. 53(5):1184-1189 (1982).

De Blasi et al., "Noninvasive measurement of forearm blood flow and oxygen consumption by near-infrared spectroscopy," J. Appl. Physiol. 76(3): 1388-1393 (1994).
De Blasi et al., "Comparison of two methods of measuring forearm oxygen consumption (VO2) by near infrared spectroscopy," J. Biomed. Optics 2: 171-175 (1997).
Doornbos et al., "The determination of in vivo human tissue optical properties and absolute chromophore concentrations using spatially resolved steady-state diffuse reflectance spectroscopy," Phys. Med. Biol. 44: 967-981 (1999).
Forbes et al., "Effects of hyperventilation on phosphocreatine kinetics and muscle deoxygenation during moderate-intensity plantar flexion exercise," J. Appl. Physiol. 102(4): 1565-1573 (2006).
Girardis et al., "Muscle perfusion and oxygen consumption by near-infrared spectroscopy in septic-shock and non-septic-shock patients," Intensive Care Medicine 29(7): 1173-1176 (2003).
Grassi et al., "Muscle $O_2$ uptake kinetics in humans: implications for metabolic control," J. Appl. Physiol. 80: 988-998 (1996).
Grassi et al., "Blood lactate accumulation and muscle deoxygenation during incremental exercise," J. Appl. Physiol. 87: 348-355 (1999).
Higginbotham et al., "Determinants of Variable Exercise Performance Among Patients with Severe Left Ventricular Dysfunction," Am. J. Cardiol. 51: 52-60 (1983).
Homma et al.,"Influence of Adipose Tissue Thickness on Near Infrared Spectroscopic Signals in the Measurement of Human Muscle," J. Biomed. Opt. 1: 418-424 (1996).
Hunter et al., "Haemoglobin oxygenation of a two-layer tissue-stimulating phantom from time-resolved reflectance: effect of top layer thickness," Phys. Med. Biol. 47: 193-208 (2002).
Juel et al., "Effect of high-intensity intermittent training on lactate and H+ release from human skeletal muscle," Am. J. Physiol. Endocrinol. Metab. 286: E245-E251 (2004).
LaFrance et al., "Near-infrared spectroscopic measurement of lactate in human plasma," Appl. Spectroscopy 54: 300-304 (2000).
Lin et al., "Influence of a fat layer on muscle oxygenation measurement using near-IR spectroscopy: quantitative analysis based on two-layered phantom experiments and Monte Carlo simulation," Frontiers Med. Biol. Eng. 10(1): 43-58 (2000).
Liu et al., "Noninvasive investigation of blood oxygenation dynamics of tumors by near-infrared spectroscopy," Appl. Opt. 39: 5231-5243 (2000).
Niwayama et al., "Quantitative measurement of muscle hemoglobin oxygenation using near-infrared spectroscopy with correction for the influence of a subcutaneous fat layer," Rev. Sci. Instrum. 71(12): 4571-4575 (2000).
Niwayama et al., "A 200-Channel Imaging System of Muscle Oxygenation using CW Near-Infrared Spectroscopy," IEICE Trans. Inf. Syst. E85-D(1): 115-123 (2002).
Poole et al., "Response of ventilatory and lactate thresholds to continuous and interval training," J. Appl. Physiol. 58: 1115-1121 (1985).
Poole et al., "Pulmonary and leg VO2 during submaximal exercise: implications for muscular efficiency," J. Appl. Physiol. 72: 805-810 (1992).
Schenkman et al., "Improved myoglobin saturation measurement made by partial least-squares analysis of optical reflectance spectra," Appl. Spectroscopy 56(9): 1215-1221 (2002).
Shao et al., "Theoretical and experimental studies on linear and nonlinear algorithms for the measurement of muscle oxygenation using continuous-wave near-infrared spectroscopy," Opt. Eng. 40(10): 2293-2301 (2001).
Shear et al., "Multivariate calibration with slowly responding reference measurements," Proc. SPIE 6007: 125-132 (2005).
Soller et al., "Investigation of electrolyte measurement in diluted whole blood using spectroscopic and chemometric methods," Appl. Spectroscopy 57: 146-151 (2003).
Soller et al., "Noninvasive, near infrared spectroscopic-measured muscle pH and $PO_2$ indicate tissue perfusion for cardiac surgical patients on cardiopulmonary bypass," Crit. Care Med. 31(9): 2324-2331 (2003).
Soller et al., "Noninvasive measurement of venous pH in septic patients: preliminary results," Crit. Care Med. 34(12 Suppl.), A55 (2006).

(56) References Cited

OTHER PUBLICATIONS

Soller et al., "Noninvasive muscle oxygen saturation is correlated with lactate, not ScvO2, in septic patients," Crit. Care Med. 34(12 Suppl.), A54 (2006).
Soller et al., "Noninvasive Sensor for Measuring Muscle Metabolism During Exercise," dated Jan. 1, 2007, retrieved on Jul. 25, 2013 from internet address http://ntrs.nasa.gov/archive/nasa/saci.ntrs.nasa.gov/20070007299_2007005321.pdf.
Soller et al., "Noninvasive determination of exercise-induced hydrogen ion threshold through direct optical measurement," J. Appl. Physiol. 104: 837-844 (2008).
Soyemi et al., "Skin color correction for tissue spectroscopy: Demonstration of a novel approach with tissue mimicking phantoms," Appl. Spectroscopy 59: 237-244 (2005).
Sun et al., "Carbon dioxide pressure-concentration relationship in arterial and mixed venous blood during exercise," J. Appl. Physiol. 90: 1798-1810 (2001).
Svedahl et al., "Anaerobic threshold: the concept and methods of measurement," Can. J. Appl. Physiol. 28(2): 299-323 (2003).
van Beekvelt et al., "Adipose tissue thickness affects in vivo quantitative near-IR spectroscopy in human skeletal muscle," Clin. Sci. 101: 21-28 (2001).
Walz et al., "Intramuscular $PO_2$ determined by near infrared spectroscopy is an early indicator of hemodynamic instability in a lower body negative pressure model of hemorrhagic shock," Shock 26(Suppl. 1), p. 16 (2006).
Wang et al., "Which common NIRS variable reflects muscle estimated lactate threshold most closely?" Appl. Physiol. Nutr. Metabol. 31: 612-620 (2006).
Wasserman et al., "Gas exchange theory and the lactic acidosis (anaerobic) threshold," Circulation 81(1 Suppl.): II14-30 (1990).
Whipp et al., "A test to determine parameters of aerobic function during exercise," J. Appl. Physiol. Resp. Env. Ex. Physiol. 50(1): 217-221 (1981).
Yamamoto et al., "Accurate NIRS measurement of muscle oxygenation by correcting the influence of a subcutaneous fat layer," Proc. SPIE 3194: 166-173 (1998).
Yang et al., "Simultaneous correction of skin color and fat thickness for tissue spectroscopy using a two-distance fiber optic probe and orthogonalization technique," Opt. Lett. 30(17): 2269-2271 (2005).
Yang et al., "Influence of a fat layer on the near infrared spectra of human muscle: quantitative analysis based on two-layered Monte Carlo simulations and phantom experiments," Opt. Express 13: 1570-1579 (2005).
Yang et al., "Effect of skin and fat layers on the spatial sensitivity profile of continuous wave diffuse reflectance near-infrared spectra," Proc. SPIE 6007: 108-116 (2005).
Yang et al., "Removal of analyte-irrelevant variation in near infrared tissue spectra," Appl. Spectroscopy 60: 1070-1077 (2006).
Yang et al., "Noninvasive in vivo Measurement of Venous Blood pH during Exercise using NIR Reflectance Spectroscopy," Appl. Spectroscopy 61: 223-229 (2007).
Zhang et al., "Partial least-squares modeling of near-infrared reflectance data for noninvasive in vivo determination of deep-tissue pH," Appl. Spectroscopy 52(3): 400-406 (1998).
Zhang et al., "Investigation of noninvasive in vivo blood hematocrit measurement using NIR reflectance spectroscopy and partial least-squares regression," Appl. Spectroscopy 54(2): 294-299 (2000).
Office Action in Australian Patent Application No. 2008311221, dated Nov. 25, 2012.
English Translation of Office Action in Chinese Patent Application No. 200880106867.8, dated Jul. 20, 2011.
English Translation of Office Action in Chinese Patent Application No. 200880106867.8, dated Jun. 21, 2012.
European Search Report for EP Application No. 08837440.0, dated Aug. 23, 2013.
Communication Pursuant to Rules 70(2) and 70a(2) for EP Application No. 08837440.0, dated Sep. 10, 2013.
International Report on Patentability for PCT Application No. PCT/US08/69998, by Examiner Dorothee Mulhausen, dated Jan. 19, 2010.
English Translation of Office Action in Japanese Patent Application No. 2010-516301, mailed on Jul. 11, 2013.
English Translation of Office Action in Japanese Patent Application No. 2010-516301, mailed on Feb. 6, 2014.

* cited by examiner

PHYSICAL PERFORMANCE MONITORING AND MONITORS

CROSS-REFERENCE TO RELATED APPLICATIONS

This application claims priority under 35 U.S.C. §119(e) to U.S. Provisional Application Ser. No. 60/949,789, filed on Jul. 13, 2007, the entire contents of which are incorporated herein be reference.

STATEMENT AS TO FEDERALLY SPONSORED RESEARCH

This disclosure was made with Government support under National Space Biomedical Research Institute grant number SM0001. The Government has certain rights in this disclosure.

TECHNICAL FIELD

This disclosure relates to methods and devices for monitoring physical performance.

BACKGROUND

The effects of physical stress on the human body can be assessed by measuring anaerobic threshold and oxygen consumption rates during exercise. For example, both professional and non-professional athletes may attempt to quantitatively assess the effectiveness of a training regimen by measuring these parameters during periods of incremental physical exercise. Effective athletic training regimens typically increase both anaerobic thresholds and oxygen consumption rates.

The rate of oxygen consumption in human tissue can be measured by a trained operator with complex and expensive gas analysis equipment. Typically, these measurements are performed in a laboratory. In contrast, an anaerobic threshold can be determined in the field, but typically involves multiple invasive measurements (e.g., multiple blood withdrawals, typically via a finger stick to obtain a drop of blood). As a result, measuring an anaerobic threshold can be both time-consuming and uncomfortable for the subject.

SUMMARY

Disclosed herein are systems and methods for the non-invasive measurement of anaerobic thresholds and oxygen consumption rates during exercise to monitor athletic performance, e.g., athletic performance, and level of fitness. Oxygen consumption measurements provide quantitative assessments of an individual's metabolic rate.

As used herein, the "oxygen consumption rate" refers to the rate at which oxygen is removed from oxygenated blood, particularly during periods of physical activity (although oxygen consumption occurs at all times). In particular, during periods of strenuous physical activity—such as during an athletic event or training session—the rate at which oxygen is consumed from blood in muscle tissues can increase significantly, relative to the rate of oxygen consumption during periods of physical inactivity. For the purposes of this disclosure, the oxygen consumption rate in the tissue of a subject is equivalent to the oxygen uptake rate. Although the term oxygen consumption rate is more commonly used in the scientific literature and will be used throughout this disclosure, it is understood that the term "oxygen uptake rate" is synonymous with oxygen consumption rate as disclosed herein.

Furthermore, as used herein, an "anaerobic threshold" refers to the rate of oxygen consumption (or another quantity related to exercise intensity) at which the rate of change of concentration of lactate in a subject's blood increases with incrementally greater work (e.g., incrementally greater physical exertion). In other words, for a subject undergoing increasing exercise intensity up to the anaerobic threshold, the subject's blood lactate concentration increases at a rate that is approximately constant in time. Once the subject's anaerobic threshold is reached, the subject's blood lactate concentration begins to rise at an abruptly faster (although, perhaps still constant rate). Physiologically, the anaerobic threshold corresponds to the point at which the rate of lactate production in the tissue exceeds the rate at which lactate is removed, and/or there is a significant increase in the rate of $CO_2$ production.

Performance monitors measure near-infrared spectra of tissue (e.g., a human subject or an animal subject) via reflectance and/or absorbance measurements to quantitatively determine physiological parameters such as pH, blood hematocrit, and oxygen saturation of the tissues. From one or more of these parameters, an anaerobic threshold can be determined. Using these parameters and measurements of heart rate and arterial oxygen saturation, oxygen consumption rates can be determined. Using the systems and methods disclosed herein, anaerobic thresholds can be determined without performing multiple invasive measurements (e.g., serial blood withdrawals), and without inducing a subject to complete a maximum exercise regimen. Thus, oxygen consumption rates can be determined without the aid of a metabolic cart and/or sophisticated gas analysis equipment and trained operators.

The performance monitors disclosed herein can be implemented as portable monitors configured to be attached to a subject such as a human patient or an animal such as a horse or dog. For example, a portable monitor for determining one or both of an anaerobic threshold and oxygen consumption rates can be configured to be attached directly to an arm or a leg of a subject via an adjustable (e.g., elastic) strap or adhesive pad. Alternatively, or in addition, the portable monitor can be attached to a belt or waistband, e.g., of a garment, and a sensor can extend from the monitor and be attached to skin of the subject via an attachment mechanism such as an adhesive pad. A single performance monitor can be used to measure both anaerobic threshold and oxygen consumption rates, or separate performance monitors can be used to measure one or both of these quantities. Performance monitors can transmit, (e.g., wirelessly transmit) data, including physiological parameters such as anaerobic threshold and oxygen consumption rates, to a display and/or storage medium. In addition, performance monitors can transmit data over networks, including wired and wireless networks.

In general, in a first aspect, the disclosure features methods of determining an anaerobic threshold of a human or animal subject, where the methods include exposing a tissue of the subject to illumination radiation, collecting emitted radiation from the tissue, the emitted radiation including a portion of the illumination radiation reflected or transmitted from the tissue, processing the emitted radiation to form a spectrum of the tissue, and determining, based on the spectrum of the tissue, an anaerobic threshold of the subject.

Embodiments of the methods can include one or more of the following features.

The methods can include determining the anaerobic threshold based on a plurality of concentration values of an analyte in the tissue.

The methods can include determining the anaerobic threshold based on a plurality of pH values of the tissue, where each of the plurality of pH values can be obtained by measuring a spectrum of the tissue and determining a pH value from the spectrum. Determining the anaerobic threshold based on the plurality of pH values can include fitting more than one of the plurality of pH values to a mathematical equation to determine parameters of the equation, and determining the anaerobic threshold from the mathematical equation.

Determining the anaerobic threshold based on the plurality of pH values can include determining a plurality of hydrogen ion concentration values of the tissue from the plurality of pH values, fitting more than one of the plurality of hydrogen ion concentration values to a mathematical equation to determine parameters of the equation, and determining the anaerobic threshold from the mathematical equation. The mathematical equation can be of the form $$y = \begin{cases} y_1 + s_1(x - x_0), & x < x_0 \\ y_2 + s_2(x - x_0), & x > x_0 \end{cases}$$

where x is a measure of exercise intensity, $x_0$ is an adjustable parameter that corresponds to the anaerobic threshold, y is the hydrogen ion concentration, and $y_1$, $y_2$, $s_1$, and $S_2$ are adjustable parameters. The measure of exercise intensity can be a rate of oxygen consumption in the tissue.

Determining the anaerobic threshold can include determining a plurality of hydrogen ion concentration values of the tissue from the plurality of pH values, fitting more than one of the plurality of hydrogen ion concentration values to a mathematical equation to determine parameters of the equation, and determining a measure of exercise intensity at which a first derivative of the mathematical equation changes. The measure of exercise intensity can be an oxygen consumption rate.

Determining the anaerobic threshold can include determining a pH value or a hydrogen ion concentration value of the tissue that corresponds to the anaerobic threshold, and the methods can include monitoring a pH value or a hydrogen ion concentration value in the subject during a period of physical exercise.

Determining the anaerobic threshold can include determining a pH value or a hydrogen ion concentration value of the tissue that corresponds to the anaerobic threshold, and the methods can include determining a first pH value or a first hydrogen ion concentration value in the subject prior to a period of physical exercise, and determining a second pH value or a second hydrogen ion concentration value in the subject following the period of physical exercise.

The methods can include determining a pH value or a hydrogen ion concentration value of the tissue that corresponds to the anaerobic threshold, and further determining pH values or hydrogen ion concentration values in the subject at least twice during a period of physical exercise to assess whether the subject's anaerobic threshold has been reached, where the pH values or the hydrogen ion concentration values are determined at a frequency of 0.1 Hz or more.

The methods can include assessing one or both of a physical condition of the subject and an effectiveness of an exercise regimen performed by the subject based on the anaerobic threshold.

The methods can also include any of the other features or method steps disclosed herein, as appropriate.

In another aspect, the disclosure features methods of determining an oxygen consumption rate of a human or animal subject, where the methods include exposing a tissue of the subject to illumination radiation, collecting emitted radiation from the tissue, the emitted radiation including a portion of the illumination radiation reflected or transmitted from the tissue, processing the emitted radiation to form a spectrum of the tissue, and determining, based on the spectrum of the tissue, an oxygen consumption rate of the subject.

Embodiments of the methods can include one or more of the following features.

Determining the rate of oxygen consumption can include determining a difference between arterial oxygen saturation and tissue oxygen saturation in the tissue. Determining the rate of oxygen consumption can include determining a stroke volume of the subject based on a heart rate of the subject.

Determining the rate of oxygen consumption can include determining a hemoglobin concentration in the tissue. Determining the hemoglobin concentration in the tissue can include determining a hematocrit level in the tissue based on the spectrum of the tissue, and determining a hemoglobin concentration in the tissue based on the hematocrit level.

The rate of oxygen consumption in the tissue can be determined according to $$\dot{V}O_2 = SV \cdot HR \cdot C_{(a-b)}O_2$$

where $\dot{V}O_2$ is the rate of oxygen consumption in the tissue, SV is a stroke volume of the subject, HR is a heart rate of the subject, and $C_{(a-b)}O_2$ is a difference between arterial and venous oxygen content in the tissue. The difference between arterial and venous oxygen content, $C_{(a-b)}O_2$, can be calculated based on values of arterial and venous oxygen saturation in the tissue and a hemoglobin concentration in the tissue.

The methods can include determining, based on the spectrum of the tissue, an anaerobic threshold of the subject.

The methods can also include any of the other features or method steps disclosed herein, as appropriate.

In a further aspect, the disclosure features apparatus that includes a spectrometer configured to detect light emitted from a tissue of a human or animal subject and to determine a spectrum of the tissue from the detected light, and an electronic processor coupled to the spectrometer and configured to determine, based on the spectrum of the tissue, at least one of an oxygen consumption rate and an anaerobic threshold of the subject.

Embodiments of the apparatus can include one or more of the following features.

The electronic processor can be configured to determine a plurality of spectra of the tissue, determine a plurality of pH values of the tissue, where each one of the plurality of pH values can be obtained from one of the plurality of spectra, and determine the anaerobic threshold based on the plurality of pH values.

The spectrometer can include at least one light source, one or more incident light ports configured to transmit light from the at least one light source to the tissue, and one or more light receiving ports configured to transmit light from the tissue to a detector, where the one or more incident light ports and the one or more light receiving ports are enclosed in a housing that includes an attachment mechanism for attaching the housing to a portion of a subject's body.

The at least one light source can include a plurality of light emitting diodes. The at least one light source can have a full width at half maximum spectral bandwidth of 50 nm or more.

The one or more light receiving ports can include one light receiving port. The one or more incident light ports can include a first light port positioned at a first distance from the light receiving port and a second light port positioned at a second distance, shorter than the first distance, from the light receiving port. The electronic processor can be configured to correct spectral data derived from light from the first light port with spectral data derived from light from the second light port. Spectral data derived from light from the first light port can include information about the tissue and about one or more layers overlying the tissue. Spectral data derived from light from the second light port can include information about the one or more overlying layers.

The apparatus can include a communication interface in electrical communication with the electronic processor, the communication interface being configured to transmit (e.g., wirelessly transmit) signals from the electronic processor to a device over at least one of a communication link and a network. The network can be a wireless network (e.g., a mobile telephone network). The network can be the internet. The communication link can be a wireless communication link. The device can be at least one of a computer, a handheld computing device, a mobile telephone, and a display device.

The signals can include information about the subject, and the device can be a computing device configured to monitor the information about the subject.

The electronic processor can be configured to determine the rate of oxygen consumption based on a stroke volume of the subject, a heart rate of the subject, a hemoglobin concentration in the subject, and a difference between arterial and tissue oxygen saturation in the subject.

A system can include an electronic device connected to a data transmission network, and a plurality of monitoring devices, each monitoring device corresponding to the apparatus, where each monitoring device is configured to transmit information about one of multiple human or animal subjects to the electronic device over the data transmission network, the information including at least one of the oxygen consumption rate and the anaerobic threshold of the subject.

Embodiments can include one or more of the following advantages.

The performance monitors disclosed herein are portable and therefore usable in a variety of environments, including field test environments and ambulatory environments. The performance monitors eliminate the need for metabolic cart devices, which typically include a face mask and mouthpiece worn by a test subject, and are often uncomfortable and claustrophobic for test subjects. Further, the performance monitors disclosed herein perform non-invasive measurements, eliminating the need for removing blood and/or other fluids from test subjects.

In addition, the performance monitors disclosed herein are simpler and less expensive than alternative equipment for assessing oxygen consumption rates in test subjects. The performance monitors do not require highly trained operators, and provide real-time results for both local display and remote monitoring.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments are set forth in the accompanying drawings and the description below. Other features and advantages will be apparent from the description, drawings, and claims.

DESCRIPTION OF DRAWINGS

Like reference symbols in the various drawings indicate like elements.

DETAILED DESCRIPTION

Infrared reflectance and/or absorbance measurements can be performed on tissues to determine a variety of parameters that can be used to assess the general physiological condition of a subject such as a human patient. Spectrometer systems suitable for performing such measurements are disclosed, for example, in U.S. Pat. No. 7,245,373 entitled "Spectrometer System for Optical Reflectance Measurements" by Babs R. Soller et al., filed on Apr. 25, 2005, the entire contents of which are incorporated herein by reference. In general, infrared reflectance and/or absorbance measurements can be performed on tissues in living organisms (e.g., humans and/or animal subjects).

Figure 1:
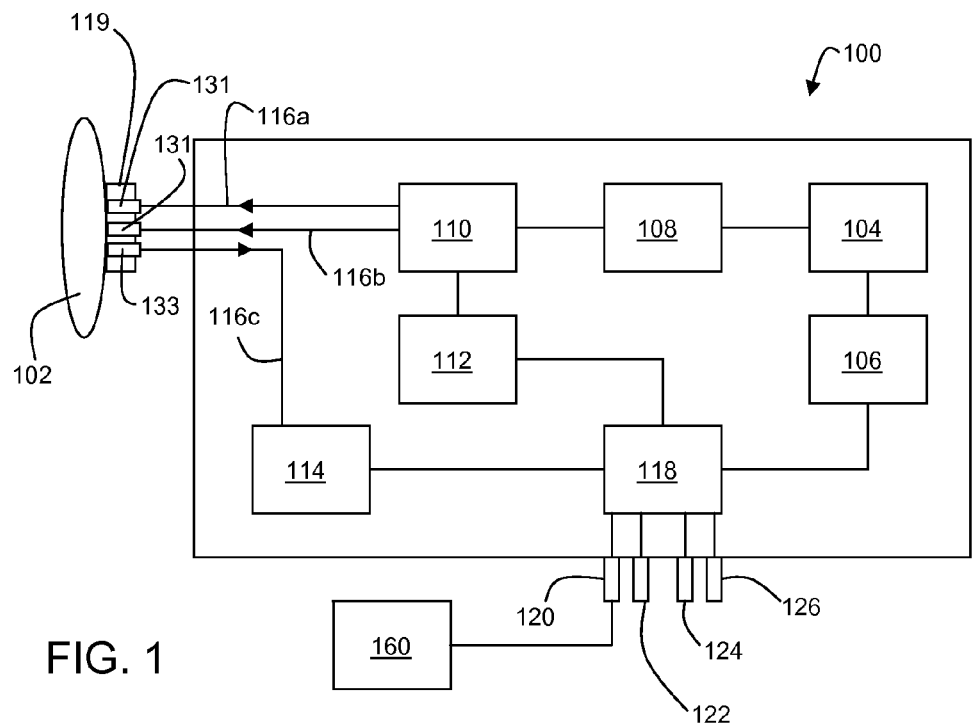
FIG. 1 is a schematic diagram of an embodiment of a performance monitor.

FIG. 1 shows an embodiment of a portable performance monitor 100 for performing reflectance and/or absorbance measurements from a tissue sample 102. Monitor 100 includes an optical source 104, a power supply 106 for source 104, an optical bench 108, a shutter system 110, a shutter system driver 112, a spectrograph 114, fiber optic cables 116a-c, a processor 118, and an attachment mechanism 119. Monitor 100 also includes a plurality of auxiliary connection ports 120, 122, 124, and 126 in electrical communication with processor 118. Four connection ports are shown schematically in FIG. 1. Embodiments of monitor 100 can have, in general, any number of auxiliary connection ports. The auxiliary connection ports permit the connection of other sensors and/or instruments to processor 118. Processor 118 can be configured to receive data from sensors and/or instruments connected to auxiliary connection ports, and processor 118 can also transmit signals to the sensors and/or instruments via the auxiliary connection ports.

Light from optical source 104 is manipulated by optical elements within optical bench 108 and can be alternately blocked and allowed to pass by shutter system 110. When light from optical source 104 passes through shutter system 110, the light is guided via fiber optic cables 116a and/or 116b to attachment mechanism 119, which is configured to secure cables 116a, 116b, and 116c to sample 102 and to permit light guided by cables 116a and/or 116b to be incident on sample 102 via one or more incident light ports 131. The incident light ports 131 provide apertures through which light coupled out of cables 116a and/or 116b passes to reach sample 102.

Light reflected and/or transmitted from sample 102 is coupled, via one or more light receiving ports 133, into fiber optic cable 116c and guided to spectrograph 114. In some embodiments, spectrograph 114 can also receive light directly from source 104 (e.g., light that has not been incident on sample 102) via another fiber optic cable (not shown in FIG. 1). Spectrograph 114, which is controlled by processor 118, determines a spectrum of light reflected from and/or absorbed by sample 102.

In certain embodiments, elements of performance monitor 100 can be combined. For example, in some embodiments, shutter system 110 and/or shutter system driver 112 can be part of optical bench 108. As another example, in some embodiments, optical source 104 can be part of optical bench 108.

Spectrograph 114 can generally be any type of device or system that permits wavelength-resolved measurement of light intensity. For example, in some embodiments, spectrograph 114 can include a dispersive element such as a diffraction grating or prism that disperses incident light spatially into a plurality of component wavelengths, and one or more optical elements to direct the component wavelengths to a detector (e.g., a CCD device, a photodiode, a photomultiplier, or another such device) configured to measure intensities of the component wavelengths. In certain embodiments, spectrograph 114 can measure intensities of component wavelengths of an incident light beam in another fashion, such as via the use of optical bandpass filters. In some embodiments, spectrograph 114 can use other elements to measure light intensity at different wavelengths.

Fiber optic cable 116a, as shown in FIG. 1, is spaced at a longer distance from fiber optic cable 116c than fiber optic cable 116b. By suitable selection of the positions of cables 116a and 116b relative to cable 116c, the spectral data measured by spectrograph 114 can be corrected to reduce or remove spectral effects due to skin and/or fat layers that overlie muscle tissues of interest in sample 102). For example, reflected light that is coupled into cable 116c and is derived from incident light directed to sample 102 from cable 116a typically includes contributions both from overlying skin and fat layers, and the deeper-lying tissue of interest (e.g., muscle tissue) in sample 102. In contrast, reflected light that is coupled into cable 116c and is derived from incident light directed to sample 102 from cable 116b typically includes (mostly) contributions from the skin and fat layers. As a result, in certain embodiments, monitor 100 can be configured to separately measure reflected light derived from incident light delivered via cables 116a and 116b, and to use the reflected light spectra derived from incident light from cable 116b to correct the spectra derived from incident light from cable 116a, to reduce and/or remove spectral contributions from the overlying skin and fat layers. Monitor 100 can also be configured to correct for variations in skin pigmentation among different subjects.

Figure 2:
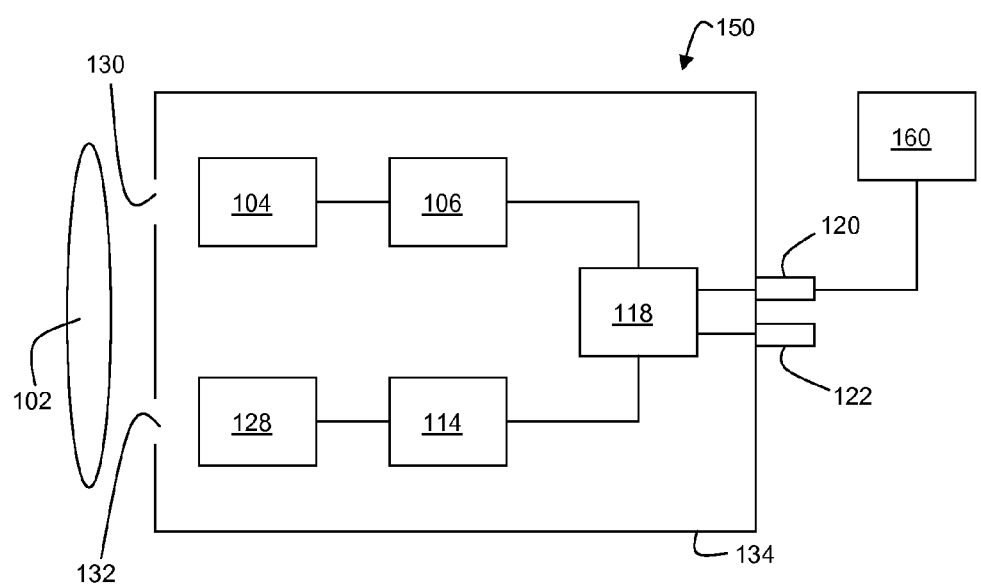
FIG. 2 is a schematic diagram of an embodiment of a performance monitor.

In some embodiments, performance monitors can include fewer components than are shown in FIG. 1, particularly where miniaturization and enhanced portability is desired. FIG. 2 shows an embodiment of a portable performance monitor 150 that includes a processor 118 with auxiliary connection ports 120 and 122, a solid-state light source 104 (e.g., light source 104 can include one or more LED sources), a light source driver 106, an optical bench 128, and a spectrograph 114. Light emitted by solid-state source 104 is incident on sample tissue 102 through an aperture 130 (or a plurality of apertures) in housing 134. Light reflected and/or transmitted from sample 102 is admitted to optical bench 128 via aperture 132 (or a plurality of apertures) in housing 134. Optical bench 128 includes optical elements that direct the reflected and/or transmitted light to spectrograph 114. Spectrograph 114, which is controlled by processor 118, determines a reflectance and/or absorbance spectrum of light from sample 102.

Typically, solid-state light source 104 provides relatively broad-bandwidth light having a full width at half maximum (FWHM) spectral bandwidth that is similar to a spectral bandwidth of the light source shown in FIG. 1 (e.g., an incandescent source). For example, in certain embodiments, a FWHM spectral bandwidth of solid-state source 104 is 1 nm or more (e.g., 3 nm or more, 5 nm or more, 10 nm or more, 30 nm or more, 50 nm or more, 75 nm or more, 100 or more, 200 nm or more, 300 nm or more, 500 nm or more, 700 nm or more, 900 nm or more).

Figure 3A:
FIG. 3A is a photograph showing an embodiment of a performance monitor.

An embodiment of a performance monitor 170 with a sensor 190 mounted on a leg 192 of a test subject via an attachment mechanism 194 is shown in FIG. 3A. Sensor 190 includes fiber optic cables configured to deliver light to leg 192, and to collect reflected light from leg 192. Monitor 170 in FIG. 3A is connected to a laptop computer 196 via a communication interface. Data from the monitor, including reflectance and/or absorbance spectra, can be transferred to the computer via the communication interface. In the embodiment shown in FIG. 3A, performance monitor 170 does not include an electronic processor—processing functions, including determining values of various parameters from the spectral data, are performed instead by computer 196. In general, the performance monitor may or may not include an electronic processor within its housing; if the monitor does not include an electronic processor within its housing, the monitor typically includes a connection (e.g., via a communication interface) to an electronic processor in an external computing device such as a desktop computer, a handheld computer, and/or a mobile telephone. The external device can perform some or all of the processing functions disclosed hereinafter, and can include a display interface for displaying values of the various parameters, for example.

Figure 3B:
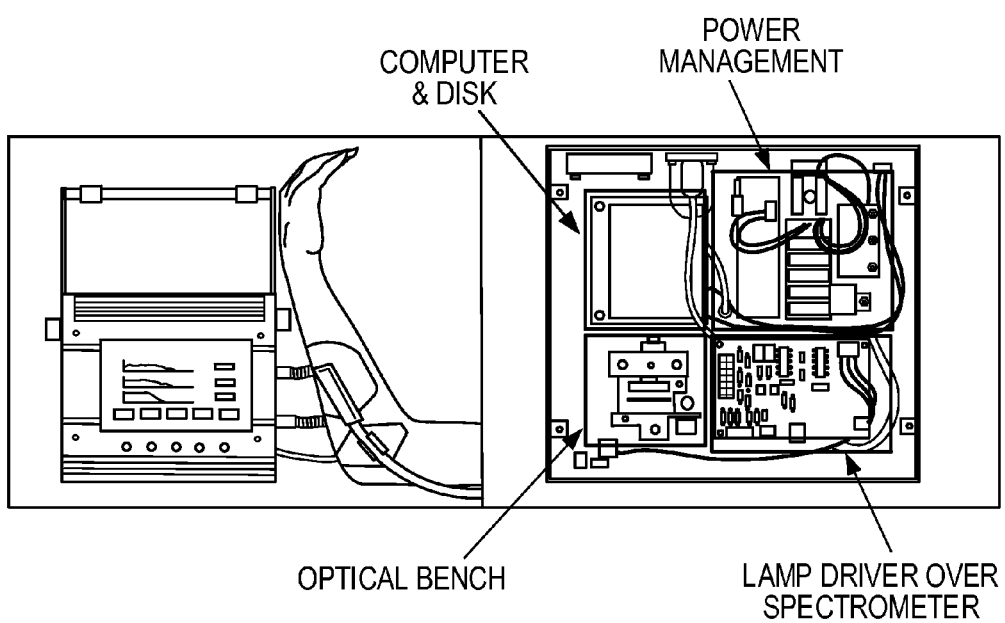
FIG. 3B is a photograph showing an internal view of a performance monitor with a processor and display positioned within the monitor housing.

FIG. 3B shows an interior view of a performance monitor similar to that shown in FIG. 3A, but including an electronic processor and a display within the monitor housing. The monitor shown in FIG. 3B measures 8"×9"×6" and weighs 8 pounds, but other dimensions and weights are also possible. For example, in some embodiments, a maximum dimension of the performance monitor is 6" or less (e.g., 5.5" or less, 5" or less, 4.5" or less, 4" or less, 3" or less, 2" or less, 1" or less, 0.5" or less, 0.25" or less). A portion of the monitor, which includes fiber optic cables and light ports enclosed by a housing, is fixed to the arm of a test subject using an attachment mechanism such as an adhesive pad. A snap connection engages the adhesive pad and the housing. In certain embodiments, other attachment mechanisms such as straps (not shown in FIG. 3B) can be used.

In addition to the display and the electronic processor, the monitor in FIG. 3B includes a storage medium, an optical bench, power control electronics, an optical source and driver, and a spectrometer. In some embodiments, the monitor can also include a battery for field use. A monitor of this size and weight can be used, for example, in field applications as well as in laboratories and training centers. Subjects undergoing study will typically be exercising (e.g., on a stationary bicycle or treadmill). For ambulatory and other uses, a miniaturized version of one of the monitors shown in FIGS. 3A and 3B can be worn on a belt, for example. Such a monitor can include, for example, a solid-state light source that provides light with a relatively side FWHM spectral bandwidth. The solid-state source can be positioned directly on the sensor (e.g., positioned within the housing attached to the subject's body). The miniaturized monitor can be powered via a battery.

Figure 14:
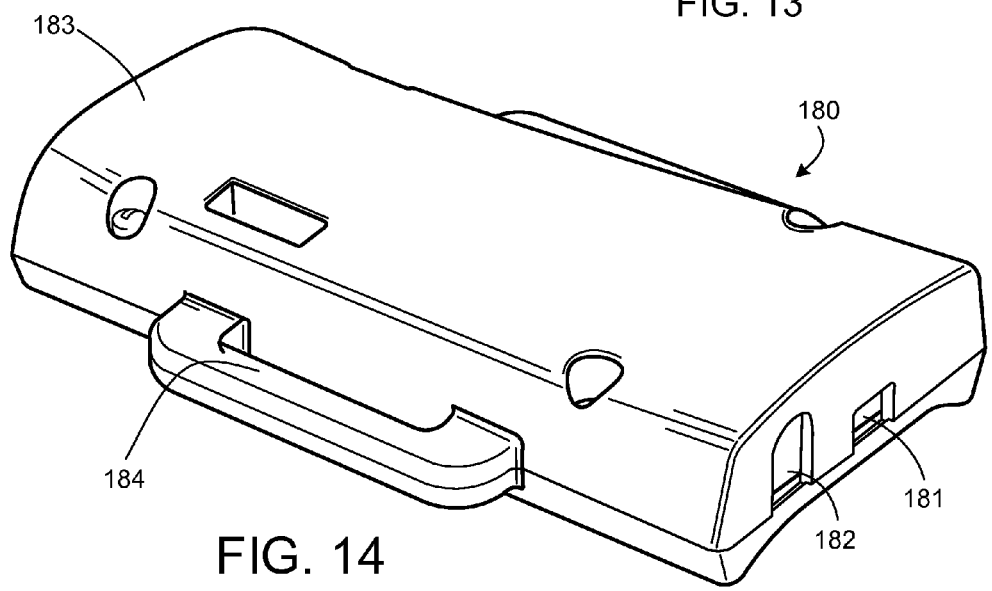
FIG. 14 is a representation of an external view of a performance monitor.

FIG. 14 shows an external view of another embodiment of a performance monitor. Monitor 180 includes a housing 183 formed of a relatively rigid material (e.g., plastic). A communications port 181 (e.g., a USB port) is configured to transmit data from monitor 180 to one or more external devices, and/or to receive data from one or more external devices. Power connector 182 is used to connect to a power source (e.g., an AC power source and/or a DC power source such as a battery). Monitor 180 can also include a separate compartment within housing 183 that is configured to house a battery so that monitor 180 can operate without being connected to a power source through port 182.

Positioned on housing 183 are connectors 184 that are configured to accommodate a fastener such as a strap, which can be used to secure monitor 180 to a subject (e.g., to a leg or arm of a subject). The fastener can include a re-fastenable closure such as a Velcro® strip that permits repeated attachment and detachment of monitor 180 from a subject.

Figure 4A:
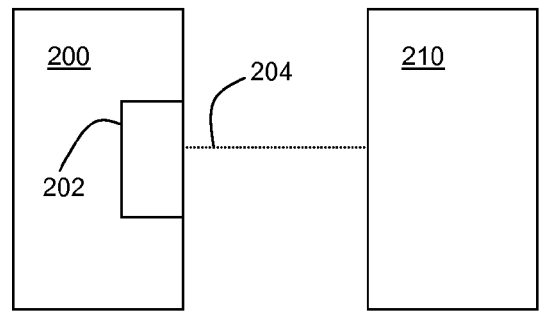
FIG. 4A is a schematic diagram of a performance monitor connected to a device via a network.

In some embodiments, performance monitors can include a communication interface for communicating with other electronic devices. A performance monitor 200 with a communication interface 202 is shown in FIG. 4A. Monitor 200 communicates with device 210 via network 204. In certain embodiments, for example, device 210 can be a computer (e.g., a desktop or notebook computer, or a handheld computer). In some embodiments, device 210 can be a mobile telephone, or another electronic device such as a display device and/or a storage device. If device 210 is a mobile telephone, device 210 can communicate with a second device (not shown) via network 204, such as a computer, and can act as a transmitting device to transmit data from monitor 200 to the second device. In general, monitor 200 can communicate with more than one device 210 via interface 202.

Network 204 can, in general, be any network that supports the exchange of signals between electronic devices. In some embodiments, for example, network 204 includes cables (e.g., coaxial cables, fiber optic cables, or other cables) that connect monitor 200 and device 210. In certain embodiments, network 204 is a wireless network such as a mobile telephone network or the internet. Monitor 200 can be configured to authenticate itself on network 204 before exchange of data is permitted between monitor 200 and device 210.

Figure 4B:
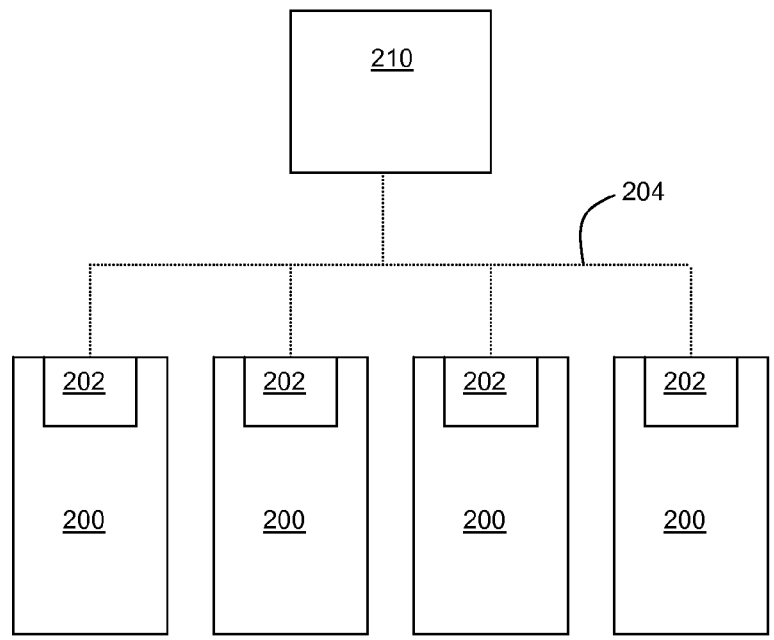
FIG. 4B is a schematic diagram of a plurality of performance monitors connected to a device via a network.

In some embodiments, a plurality of monitors can be connected to one or more electronic devices via a network. FIG. 4B shows a plurality of monitors 200, each having a communication interface 202. Each monitor is connected to device 210 via network 204, and can exchange data (e.g., data measured by monitor 200 and/or control instructions) with device 210.

Reflectance and/or absorbance spectra determined by spectrograph 114 can be processed by processor 118 to determine various physiological parameters corresponding to sample tissue 102. In some embodiments, for example, physiological parameters that can be determined from spectra can include any one or more of tissue pH (from which hydrogen ion concentration is derived), tissue oxygen saturation, blood hematocrit, blood hemoglobin concentration, tissue oxygen partial pressure, and water fraction. Systems and methods for determining each of these parameters are disclosed, for example, in the following U.S. patents and patent applications, each of which is incorporated herein by reference in its entirety: U.S. Pat. No. 5,813,403, entitled "Optical Measurement of Tissue pH," by Babs R. Soller et al., filed on Nov. 8, 1995; U.S. Pat. No. 6,006,119, entitled "Non-Invasive Optical Measurement of Blood Hematocrit," by Babs R. Soller et al., filed on Feb. 4, 1998; U.S. Pat. No. 6,766,188, entitled "Tissue Oxygen Measurement System," by Babs R. Soller, filed on Oct. 11, 2002; and U.S. Patent Application Publication No. US 2008/0097173, entitled "Measuring Tissue Oxygenation," by Olusola O. Soyemi et al., filed on May 30, 2007.

In some embodiments, the measured spectra can be corrected prior to determining physiological parameters. For example, in certain embodiments, spectra of tissue can be corrected to reduce the effects of light scattering and/or absorption by layers of skin and/or fat that overlie the muscle tissue (e.g., skin and/or fat that is positioned between the spectrometer system and the muscle tissue). Systems and methods for correcting spectra are disclosed, for example, in U.S. patent application Ser. No. 11/411,538, entitled "Systems and Methods for Correcting Optical Reflectance Measurements," by Ye Yang et al., filed on Apr. 25, 2006, now published as U.S. Publication No. US 2007/0038041, the entire contents of which are incorporated herein by reference.

Physiological parameters determined from reflectance and/or absorbance measurements can be used to determine other physiologically important quantities. In particular, parameters measured by the performance monitors disclosed herein can be used to determine an anaerobic threshold and a rate of oxygen consumption in a subject such as a human patient.

The anaerobic threshold and hydrogen ion concentration are related in tissue, because production of blood lactate during periods of exercise changes in proportion to the local pH in the tissue. As a result, lactate concentration in a sample tissue of a subject, which may be used to determine anaerobic threshold, can be monitored by measuring hydrogen ion concentration in the tissue. Hydrogen ion concentration can be determined directly from pH measurements in the tissue, where the hydrogen ion concentration [H$^+$] is related to pH mathematically as [H$^+$]=10$^{-pH}$. Tissue pH can be determined from near-infrared reflectance and/or absorbance measurements, as discussed above. As a result, the portable performance monitors disclosed herein can be used to monitor blood lactate concentration in subject tissues from near-infrared measurements performed on the tissues.

Metabolic rate is assessed herein based on the measurement of a rate of oxygen consumption by a subject. The rate of oxygen consumption ($\dot{V}O_2$) in tissue can be calculated as $$\dot{V}O_2 = Q \times [C \times [Hb] \times (Sa_{O2} - Sv_{O2})] + 0.003 \times (Pa_{O2} - Pv_{O2}) \quad (1)$$

where Q is a cardiac output of the subject, C is a numerical constant or a numerical function, [Hb] is the hemoglobin concentration, $Sa_{O2}$ and $Sv_{O2}$ are the values of arterial and tissue oxygen saturation corresponding to oxygen bound to hemoglobin in the tissue, and $Pa_{O2}$ and $Pv_{O2}$ are the partial pressures of arterial and tissue oxygen that are not bound to hemoglobin in the tissue. Typically, C has a constant value of 1.34, which corresponds to a typical volume of oxygen (in mL) per gram of hemoglobin in tissue. In general, however, C can have other values depending upon the environmental and measurement conditions. In some embodiments, for example, C may not even be a constant. That is, C can be a function of various measurement conditions. For example, C can be a function that returns a value that is scaled according to changes in a subject's stroke volume. The cardiac output Q is equal to the product of stroke volume (SV) and heart rate (HR). Typically, the second term in Equation (1) is small in magnitude relative to the first term, and can be neglected.

In some embodiments, near-infrared reflectance and/or absorbance measurements can be used to determine a relative value of $\dot{V}O_2$ that is normalized by the subject's stroke volume, $\dot{V}O_2$ (NIRS). The quantity $\dot{V}O_2$ (NIRS) is proportional to $\dot{V}O_2$ (e.g., corresponding to a relative oxygen consumption rate) and provides a measure of oxygen consumption rates in a subject's tissue. Mathematically, $\dot{V}O_2$ (NIRS) can be determined from quantities derived from near-infrared spectral measurements according to $$\dot{V}O_2(NIRS) = 1.34 \cdot HR \cdot [Hb] \cdot (Sa_{O2} - Sv_{O2}) \quad (2)$$

where HR is a heart rate of the subject, [Hb] is a hemoglobin concentration in the tissue of the subject, $Sa_{O2}$ is arterial oxygen saturation, and $Sv_{O2}$ is tissue oxygen saturation. The quantities in Equation (2) can be measured directly or derived from a variety of measurements including near-infrared reflectance and/or absorbance measurements and standard pulse oximetry measurements, so that $\dot{V}O_2$ (NIRS) can be determined directly from spectroscopic measurements.

For example, heart rate (HR) and arterial oxygen saturation (SaO$_2$) can be determined using standard pulse oximetry measurements. These measurements can be obtained using a separate commercially available finger, forehead or ear pulse oximeter sensor (e.g., the Nellcor OxyMax™ Fast Forehead Sensor and pulse oximeter system available from Nellcor, Pleasanton, Calif.) that connects to one of the auxiliary ports on the performance monitors disclosed herein. A pulse oximeter sensor 160 is shown schematically in FIGS. 1 and 2, connected to processor 118 through auxiliary port 120. Alternatively, or in addition, the performance monitors disclosed herein can include appropriate sensors and processing software to perform pulse oximetry-based measurements of HR and SaO$_2$ directly from the collected near-infrared spectra.

Hemoglobin concentration [Hb] can be estimated as one third of the hematocrit level determined from near-infrared spectra; the performance monitors disclosed herein are configured to measure hematocrit level directly, as discussed above. Alternatively, or in addition, the hemoglobin concentration can be determined directly from near-infrared spectral measurements.

Muscle oxygen saturation (Sm$_{O2}$) is approximately equal to venous (e.g., tissue) oxygen saturation (Sv$_{O2}$), and the performance monitors disclosed herein are configured to measure tissue oxygen saturation from reflectance and/or absorbance measurements by directly determining muscle oxygen saturation.

In some embodiments, near-infrared spectral measurements can be used to directly determine an absolute (e.g., rather than a relative) rate of oxygen consumption in the tissue of a subject. The absolute rate of oxygen consumption $\dot{V}O_2$ (abs) can be estimated from the Fick equation according to $$\dot{V}O_2(abs) = SV \times HR \times C_{(a-v)}O_2 \quad (3)$$

where SV is the stroke volume, HR is the heart rate, and $C_{(a-v)}O_2$ is a difference between arterial (a) and venous (v) oxygen content. The difference between arterial and venous oxygen content can be calculated according to $$C_{(a-v)}O_2 = \frac{(Sa_{O2} - Sv_{O2})}{100} \times 1.34 \times [Hb] \times 10 + (0.003 \times (Pa_{O2} - Pv_{O2})) \quad (4)$$

where [Hb] is the hemoglobin concentration, $Sa_{O2}$ and $Sv_{O2}$ are the values of arterial and venous (e.g. tissue) oxygen saturation corresponding to oxygen bound to hemoglobin in the tissue, and $Pa_{O2}$ and $Pv_{O2}$ are the partial pressures of oxygen that is not bound to hemoglobin in the tissue. Typically, the second term in Equation (4) is small in magnitude relative to the first term, and can be neglected.

Near-infrared reflectance and/or absorbance measurements can be used to estimate an absolute oxygen consumption rate $\dot{V}O_2$ (abs) in tissue of a subject according to Equations (3) and (4) above. Each of the quantities in Equations (3) and (4) above can be measured directly or derived from a variety of measurements including near-infrared reflectance and/or absorbance measurements and standard pulse oximetry measurements, so that $\dot{V}O_2$ (abs) can be determined directly from spectroscopic measurements. For example, as discussed above, heart rate (HR) and arterial oxygen saturation (Sa$_{O2}$) can be determined using standard pulse oximetry measurements, using a separate commercially available finger, forehead or ear pulse oximeter sensor. Alternatively, or in addition, the performance monitors disclosed herein can include appropriate sensors and processing software to perform measurements of HR and SaO$_2$ directly from the collected near-infrared spectral data.

Also as discussed above, hemoglobin concentration [Hb] can be estimated as one third of the hematocrit level determined from near-infrared spectra; the performance monitors disclosed herein can be configured to measure hematocrit level directly, and to determine [Hb] from the hematocrit level. Alternatively, the performance monitors can be configured to determine hemoglobin concentration directly from near-infrared spectra.

Muscle oxygen saturation (Sm$_{O2}$) is approximately equal to venous (e.g., tissue) oxygen saturation (Sv$_{O2}$) as discussed previously, and the performance monitors can be configured to measure tissue oxygen saturation from reflectance and/or absorbance measurements by directly determining muscle oxygen saturation.

A variety of different methods can be used to determine stroke volume (SV). In some embodiments, for example, stroke volume can be measured directly using equipment that interfaces with the performance monitors disclosed herein. In certain embodiments, stroke volume can be determined from measurements of heart rate. Krip et al., Med. Sci. Sports Exerc. 29: 1469-1476 (1997), notes that a relationship exists between stroke volume and heart rate. The performance monitors disclosed herein can be configured to determine stroke volume (SV) based on heart rate (HR) according to the equation $$SV = D[1 - e^{-A(HR-B)}] \quad (5)$$

where A, B, and D are adjustable parameters. Values of parameters A, B, and D can be determined by estimating SV values from resting echocardiograms using the method of Krip et al., and fitting the estimated SV values to corresponding measured HR values in a regression analysis to determine values of A, B, and D. Values of these parameters (and/or, in certain embodiments, the form of Equation (5)) can be adjusted to account for differences in gender among different subjects. For example, parameters A and B can take the numerical values 0.0132 and 27.45, respectively, while parameter D, which corresponds to stroke volume at a maximum rate of oxygen consumption, can take the value 0.154 for male subjects and 0.096 for female subjects.

An anaerobic threshold is generally defined herein as the value of $\dot{V}O_2$ or another quantity related to exercise intensity where the first derivative of a lactate concentration curve corresponding to lactate in the blood increases with incrementally greater work (e.g., incrementally greater physical exertion). To determine the anaerobic threshold, measured values of a quantity that is related to lactate concentration are analyzed with a simultaneous bilinear regression using the fitting equation $$y = \begin{cases} y_1 + s_1(x - x_0), & x < x_0 \\ y_2 + s_2(x - x_0), & x > x_0 \end{cases} \quad (6)$$

where $s_1$ and $s_2$ are the slopes of the two linear segments of the bilinear fitting curve, $y_1$ and $y_2$ are intercepts of the two linear segments of the bilinear fitting curve, x corresponds to a quantity related to exercise intensity such as $\dot{V}O_2$, and $x_0$ is the value of $\dot{V}O_2$ (or another quantity related to exercise intensity) where the first derivative of y vs. $\dot{V}O_2$ (or another quantity related to exercise intensity) changes. The quantity y is related to lactate concentration, and typically corresponds to measured data for the tissue of interest. For example, y can correspond to measured lactate concentration in the blood, to measured hydrogen ion concentration in the tissue, or to a rate of carbon dioxide production in the lungs. The value $x_0$, which is common to both segments in the bilinear fitting equation, is also referred to as the anaerobic threshold, and represents the point at which the rate of lactate production in the tissue exceeds the rate at which lactate is removed, the hydrogen ion concentration begins to increase, and/or there is a significant increase in the rate of $CO_2$ production. Typically, the anaerobic threshold represents the highest steady-state exercise intensity that a subject can maintain for prolonged periods (several minutes, for example).

The anaerobic threshold can also be determined using equations other than Equation (6) above to fit values of the quantity y. In general, an anaerobic threshold can be determined using any fitting algorithm that accurately determines value $x_0$ from the measured values of quantity y.

The performance monitors disclosed herein can be used in a wide variety of applications due to their portability and non-invasive nature. For example, performance monitors can be used to assess the effectiveness of athletic training regimens, because effective regimens should increase both a subject's anaerobic threshold and rate of oxygen consumption. Performance monitors can also be used in fitness clubs to monitor individuals who are exercising, both to assess the effective of training regimens and to ensure that the health of exercising individuals is not compromised. For example, performance monitors can be used to help design and monitor exercise programs for overweight and obese individuals. The effectiveness of rehabilitation regimens, as with athletic training regimens discussed above, can be assessed via measurements of oxygen consumption rates and the anaerobic threshold provided by the performance monitors disclosed herein. The performance of racing animals, such as horses and dogs, can also be monitored.

In addition, performance monitors can be used in restricted environments to monitor the health of subjects who may experience adverse physical conditions. For example, performance monitors can be used to monitor the health of firefighters in flame-retardant suits, environmental hazard workers in hazardous material suits, responders to biological and chemical warfare events, workers in protective suits handling dangerous biological materials, and other workers performing strenuous physical work and wearing suits that provide a closed environment that is not easily accessible to standard health monitoring devices.

A further application of the performance monitors disclosed herein to persons working in restricted-access environments is to astronauts wearing spacesuits. Spacesuits are complex systems of garments, equipment, and environmental systems to keep humans alive in space. When an astronaut is working on a lunar surface, for example, he/she must have adequate oxygen, cooling water, and filters to remove $CO_2$ from the suit over a period of hours. During the Apollo lunar missions, a Metabolic Assessment Team of physiologists at Mission Control on earth analyzed data reported back from suit sensors to advise astronauts on how their activities were impacting the consumable resources within the suit. The most important parameter for this assessment was metabolic rate (e.g., rate of energy produced as heat, in cal/min). Approximately 200 mL of oxygen are consumed for every calorie of heat produced.

Typically, metabolic rate is assessed by measuring oxygen consumption rate. However, standard methods of measuring oxygen consumption rates—which include measurement of expired gases with a mask or mouthpiece worn by a subject—may not be accurate, and may not be compatible with oxygen-rich, closed spacesuit environments. The performance monitors disclosed herein can be adapted for use in closed environments such as spacesuits, and permit continuous (or nearly-continuous), non-invasive, and relatively unobtrusive monitoring of oxygen consumption rate and determination of metabolic rate for astronauts. Monitors for use in spacesuits can include multiple sensors to provide for redundancy in the event that individual sensors fail. For example, the monitors can include a sensor on each leg of the astronaut. The monitors can also include a reflectance-based pulse oximeter as part of the sensor for performing heart rate measurements.

Another application for the performance monitors disclosed herein is in pre-operative assessment and rehabilitation. Non-invasive measurements can be used to determine whether a candidate for surgery is likely to survive the surgery based on aerobic capacity, which can be assessed from measurements of oxygen consumption rates and/or anaerobic thresholds. For example, for elderly subjects undergoing major intra-abdominal surgery, an anaerobic threshold has been shown to be a good predictor of mortality from cardiopulmonary causes in the postoperative period. Pre-operative screening by measuring an anaerobic threshold has been shown to permit the identification of high-risk subjects and appropriate selection of perioperative management. In particular, in one reported study, 548 subjects aged 60 or older, having known cardiopulmonary disease, and scheduled for major intra-abdominal surgery, were assigned to one of three management strategies (ICU, HDU, or ward) based on an anaerobic threshold and echocardiography evidence of myocardial ischemia as determined by cardiopulmonary exercise (CPX) testing that was performed as part of pre-surgery assessment. An overall subject mortality rate was 3.9%, from which 43% of deaths were attributed to poor cardiopulmonary function, as detected pre-operatively based on anaerobic threshold measurements. There were no deaths related to cardiopulmonary complications in any subject deemed fit for surgery and ward management based on anaerobic threshold measurements. Results of the study are disclosed in Older, Paul et al., "Cardiopulmonary Exercise Testing as a Screening Test for Perioperative Management of Major Surgery in the Elderly," Chest 116: 355-362 (1999), the entire contents of which are incorporated herein by reference. Performance monitors disclosed herein can be used for pre-operative assessments of subjects, with the added advantage that an anaerobic threshold can be measured using a sensor or sensors on a leg of a subject walking on a treadmill or cycling. The surgical candidate is not required to wear a mask or exposed to other cumbersome measurement equipment.

Pre-operative assessment via measurements of an anaerobic threshold and/or an oxygen consumption rate is also disclosed in the following references, the entire contents of each of which are incorporated herein by reference: Whipp, Brian J., "Physiological mechanisms dissociating pulmonary $CO_2$ and $O_2$ exchange dynamics during exercise in humans,"Experimental Physiology, 92: 347-355 (2007); Gitt, A. et al., "Exercise anaerobic threshold and ventilatory efficiency identify heart failure patients for high risk of early death," Circulation, 106: 3079-3084 (2002); Casaburi, R. et al., "Reductions in exercise lactic acidosis and ventilation as a result of exercise training in patients with obstructive lung disease,"Am. Rev. Respir. Dis., 143: 9-18 (1991); Older, P. et al., "Preoperative evaluation of cardiac failure and ischemia in elderly patients by cardiopulmonary exercise testing," Chest, 104: 701-704 (1993); and Wasserman, K. et al., *Principles of Exercise Testing and Interpretation*, 4th edition, Lea & Febiger (Philadelphia, Pa.).

Other applications include local and/or remote monitoring of subjects. For example, the performance monitors disclosed herein can be used to monitor subjects in a patient care facility such as a hospital or retirement home. Various physiological parameters can be measured by monitors worn by the subjects, and electronic signals that include one or more of the various parameters can be transmitted to a central monitoring facility. Similarly, monitors can be worn by subjects in a hospital, and can transmit information about the subjects to another monitoring device (e.g., a device that also monitors signals from other instruments) or to a centralized monitoring station such as a nursing station.

Processing Hardware and Software

The steps described above in connection with various methods for collecting, processing, analyzing, and interpreting information from samples can be implemented in computer programs using standard programming techniques. Such programs are designed to execute on programmable computers or specifically designed integrated circuits, each comprising an electronic processor, a data storage system (including memory and/or storage elements), at least one input device, and least one output device, such as a display or printer. The program code is applied to input data (e.g., spectral data from the detector) to perform the functions described herein and generate output information (e.g., physiological parameters and quantities derived therefrom, including anaerobic threshold values and oxygen consumption rates), which is applied to one or more output devices. Each such computer program can be implemented in a high-level procedural or object-oriented programming language, or an assembly or machine language. Furthermore, the language can be a compiled or interpreted language. Each such computer program can be stored on a computer or machine readable storage medium (e.g., CD ROM or magnetic diskette) that when read by a computer or other machines can cause the processor in the computer to perform the analysis and control functions described herein.

EXAMPLES

The disclosure is further described in the following examples, which are not intended to limit the scope of the disclosure described in the claims.

To evaluate the ability of the performance monitors disclosed herein to measure anaerobic threshold and oxygen consumption rates in subjects, a test study was performed on a group of ten human subjects (five males and five females). Each subject performed a maximal cycle ergometry protocol (exercise intensity increasing in 50 W increments every 3 minutes). Subjects stopped the test when they could no longer cycle at the required cadence. Near-infrared spectra were collected every ten seconds from the vastus lateralis (thigh) muscle using a performance monitor similar to the monitor shown in FIG. 3A. The spectra were corrected for variations due to skin pigmentation and overlying fat layers.

Measurements of $\dot{V}O_2$ and carbon dioxide production during the exercise regimen were performed using a metabolic cart (model True One 2400, obtained from Parvo Medics, Salt Lake City, Utah). Heart rate measurements were performed with a Polar heart rate monitor (available from Polar USA, Long Island, N.Y.). During the final 30 seconds of each stage of the regimen, a small blood sample was obtained from a fingertip of each subject for measurement of blood lactate using an external monitor (model YSI 1500 SPORT, available from YSI Life Sciences, Yellow Springs, Ohio).

Figure 15:
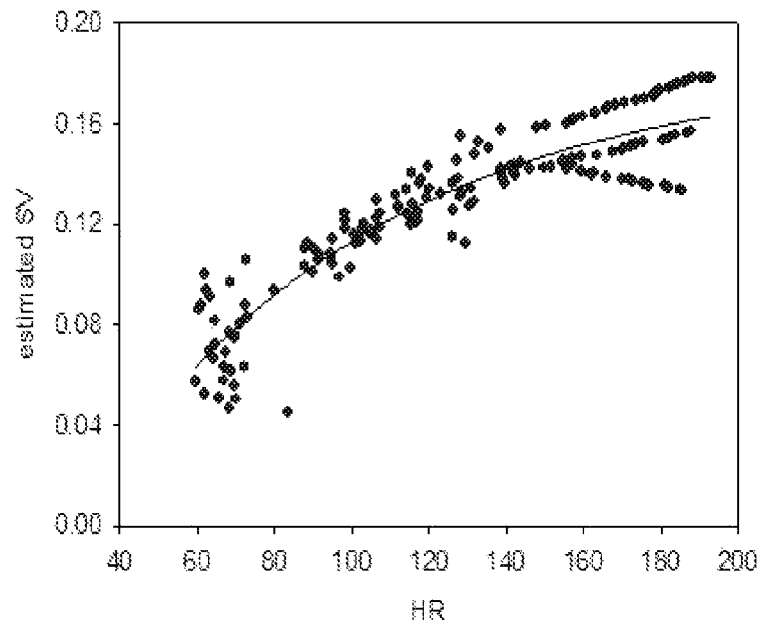
FIG. 15 is a plot of estimated stroke volume as a function of heart rate for three test subjects.

Values of $[H^+]$ (e.g., pH), hematocrit, and muscle oxygen saturation were determined for each subject from near-infrared spectral measurements. The stroke volume for each subject during exercise was estimated from heart rate measurements. From resting echocardiograms, and based on Krip et al.'s method, stroke volume values were estimated for three of the ten subjects. The estimated stroke volume values were fitted as a function of measured heart rate values to Equation (5), and values were determined for parameters A, B, and D. These parameter values were modified according to subject gender; for both male and female subjects, the values of A and B were determined to be 0.0132 and 27.45, respectively. For male subjects, the value of D was determined to be 0.154, and for female subjects, the value of D was determined to be 0.096. FIG. 15 shows a plot where estimated SV values (e.g., from echocardiograms) are plotted against measured HR values. The solid line in FIG. 15 corresponds to the equation of best-fit that determines parameter values A, B, and D.

Relative values of the oxygen consumption rate, $\dot{V}O_2$ (NIRS), were determined for each of the subjects according to Equations (1) and (2), using the methods discussed above. Further, absolute values of the oxygen consumption rate, $\dot{V}O_2$ (abs), were determined for each of the subjects according to Equations (3)-(5), using the methods discussed above.

Figure 5:
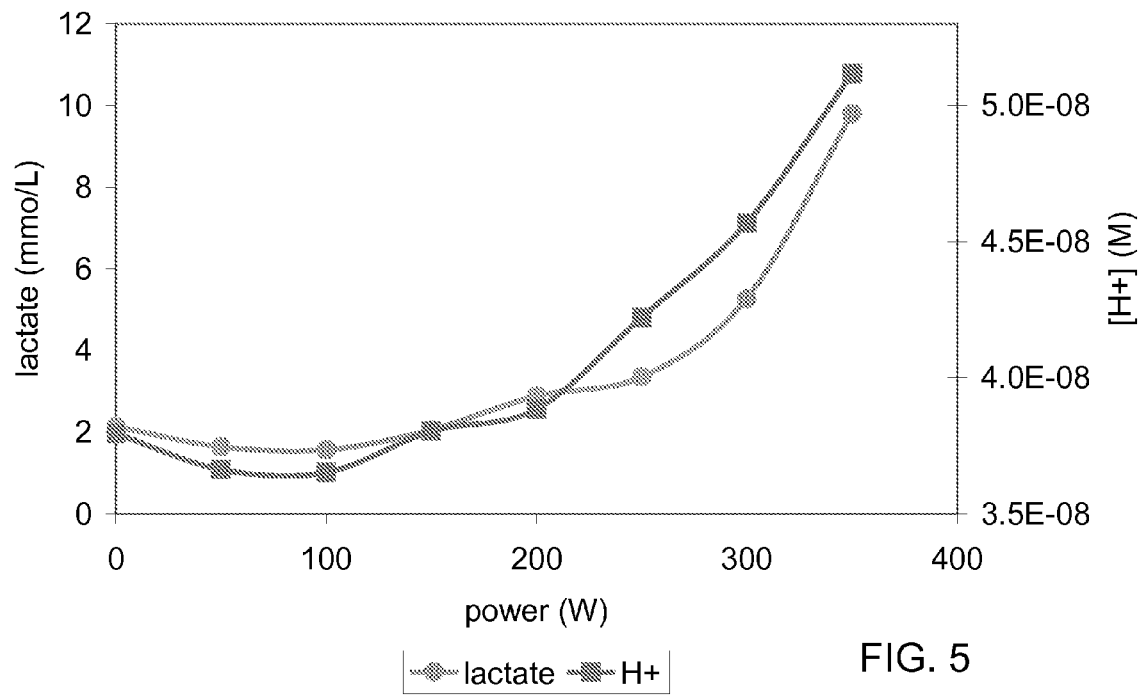
FIG. 5 is a plot of lactate concentration and hydrogen ion concentration as a function of exercise intensity for a test subject.

A graph comparing measured values of blood lactate (external monitor, ●) and measured values of [H⁺] (near-infrared measurements using the performance monitor, ■) for one test subject is shown in FIG. 5. Table 1 provides values of the correlation coefficient, $R^2$, between the [H⁺] and blood lactate measurements for nine of the test subjects. The average $R^2$ value for the nine subjects was 0.88.

TABLE 1

| Subject | $R^2$ |
|---------|-------|
| 1 | 0.89 |
| 2 | 0.95 |
| 3 | 0.94 |
| 4 | 0.71 |
| 5 | 0.92 |
| 6 | 0.72 |
| 7 | 0.95 |
| 8 | 0.88 |
| 9 | 0.93 |
| Average | 0.88 |

Figure 6:
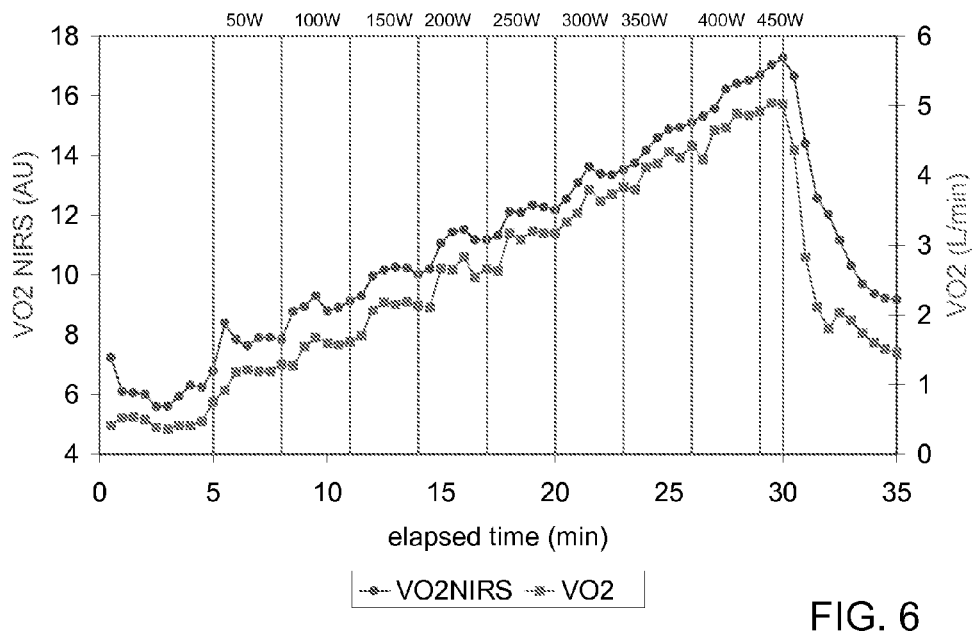
FIG. 6 is a plot of oxygen consumption rate measured via near infrared spectroscopy and via standard instrumentation as a function of time for a first test subject.
Figure 7:
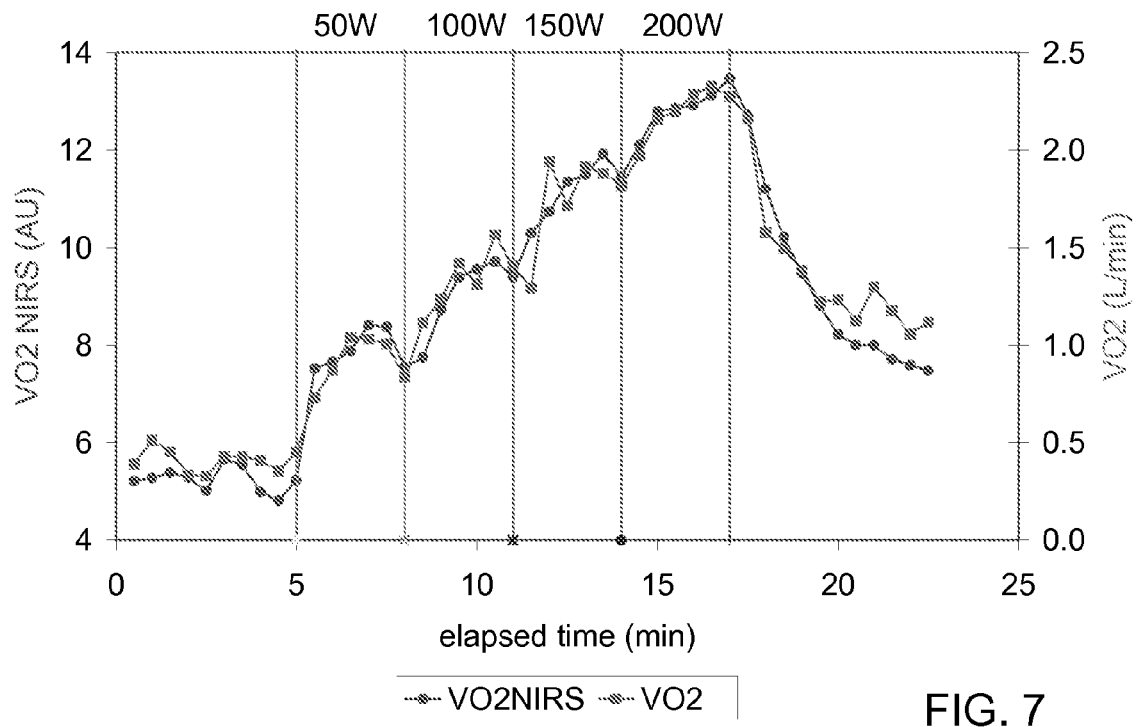
FIG. 7 is a plot of oxygen consumption rate measured via near infrared spectroscopy and via standard instrumentation as a function of time for a second test subject.

For the same test subjects, values of $\dot{V}O_2$ measured using the metabolic cart were compared to values of $\dot{V}O_2$ (NIRS) derived from near-infrared measurements performed by the monitor. Graphs comparing measured values of $\dot{V}O_2$ (■) and $\dot{V}O_2$ (NIRS) (●), measured as a function of time during the exercise protocol for two different subjects are shown in FIGS. 6 and 7, respectively. The correlation between values of $\dot{V}O_2$ and $\dot{V}O_2$ (NIRS) for each of the subjects in FIGS. 6 and 7 was relatively consistent over the 35-minute duration of the test. Note that $\dot{V}O_2$ (NIRS) was measured in arbitrary units because the absolute value of stroke volume was not known, which accounts for the differing offsets between the curves in FIGS. 6 and 7. Table 2 provides values of the correlation coefficient between measured values of $\dot{V}O_2$ and $\dot{V}O_2$ (NIRS) for each of the ten subjects. The average $R^2$ value for the ten subjects was 0.96.

TABLE 2

| Subject | $R^2$ |
|---------|-------|
| 1 | 0.98 |
| 2 | 0.98 |
| 3 | 0.95 |
| 4 | 0.96 |
| 5 | 0.96 |
| 6 | 0.96 |
| 7 | 0.97 |
| 8 | 0.96 |
| 9 | 0.93 |
| 10 | 0.97 |
| Average | 0.96 |

For monitoring subjects during periods of physical stress (e.g., during exercise), measurements of $\dot{V}O_2$ (NIRS) may be sufficient. Athletic training regimens, for example, are expected to improve a subject's maximum value of $\dot{V}O_2$ (NIRS), so that the effectiveness of the regimen can be monitored directly via measurements of $\dot{V}O_2$ (NIRS).

In some embodiments, however, the performance monitor can be configured to determine $\dot{V}O_2$ in absolute units (e.g., liters of $O_2$ per minute). In certain embodiments, measurements of $\dot{V}O_2$ and $\dot{V}O_2$ (NIRS) can be compared, and a mathematical relationship (e.g., a statistical relationship) between the two different measurements can be derived from the comparison. For example, a regression equation can be derived from measurements of $\dot{V}O_2$ and $\dot{V}O_2$ (NIRS) (e.g., based on a correlation between the values of $\dot{V}O_2$ and $\dot{V}O_2$ (NIRS) in FIG. 6 and/or FIG. 7), so that the regression equation permits calculation of $\dot{V}O_2$ from a measured value of $\dot{V}O_2$ (NIRS).

Figure 16:
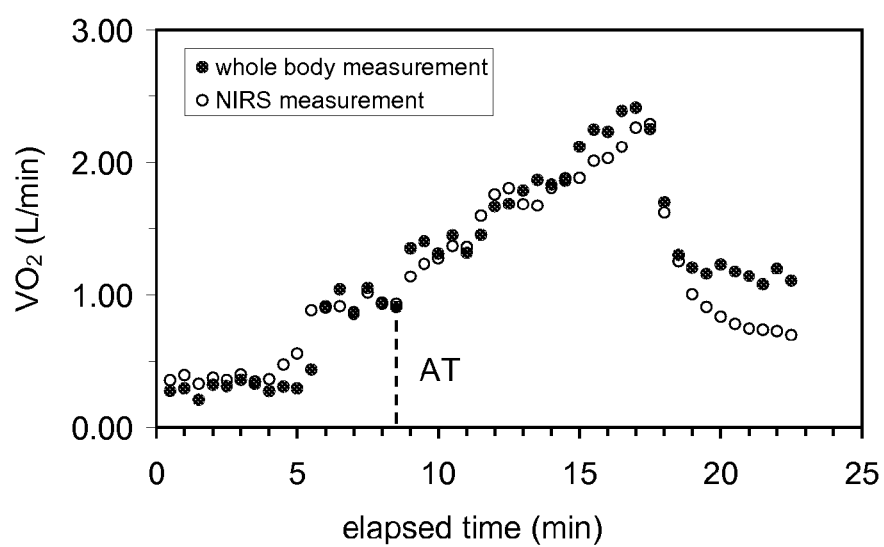
FIG. 16 is a plot of absolute oxygen consumption rate, determined from whole body measurements and near-infrared spectral measurements, as a function of time for a female test subject.
Figure 17:
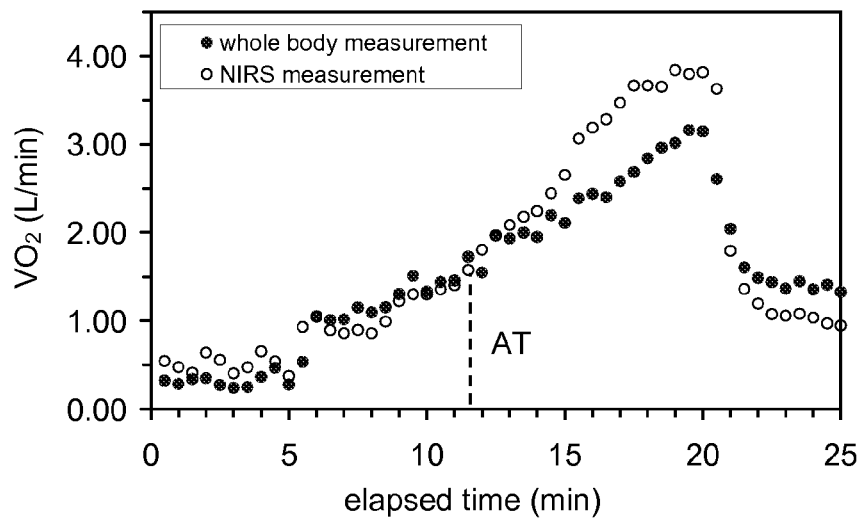
FIG. 17 is a plot of absolute oxygen consumption rate, determined from whole body measurements and near-infrared spectral measurements, as a function of time for a male test subject.
Figure 18:
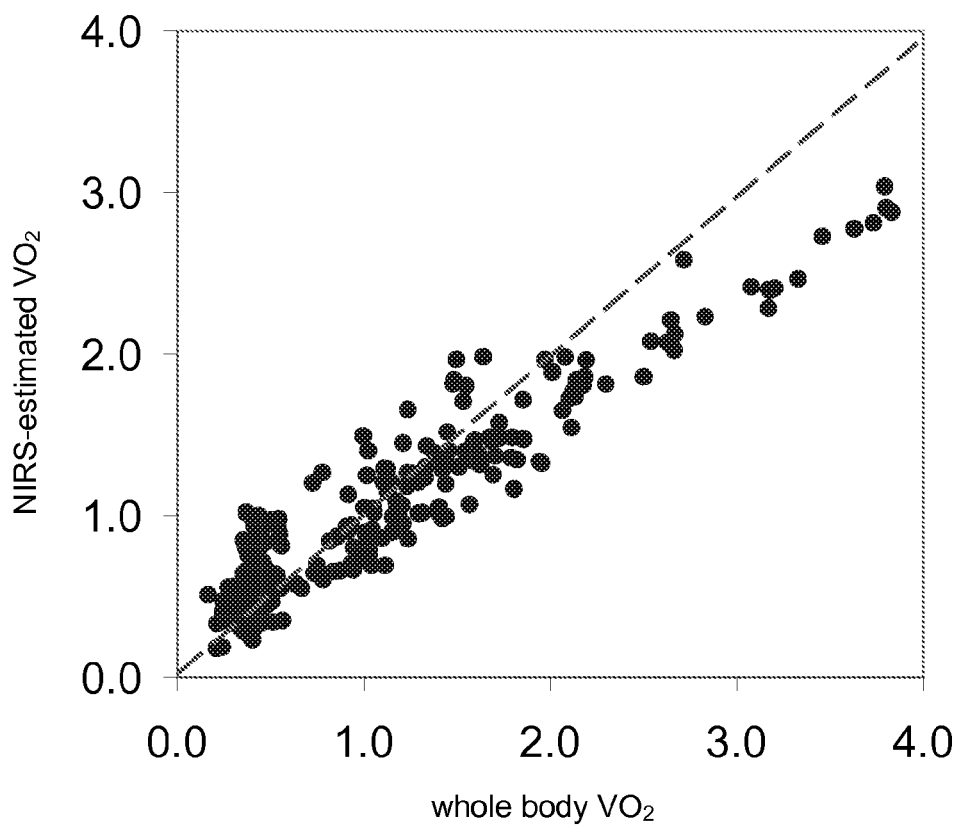
FIG. 18 is a plot showing a correlation between oxygen consumption rates determined from whole body measurements and from near-infrared spectral measurements.

As discussed above, the performance monitors disclosed herein can be configured to determine absolute oxygen consumption rates, $\dot{V}O_2$ (abs), in a subject's tissues based on Equations (3)-(5), and $\dot{V}O_2$ (abs) was determined for each of the ten subjects. FIGS. 16 and 17 show direct measurements of whole body $\dot{V}O_2$ and $\dot{V}O_2$ (abs) for two different subjects, a female (FIG. 16) and a male (FIG. 17), as a function of time during the test protocol. Good agreement was obtained between whole body $\dot{V}O_2$ and $\dot{V}O_2$ (abs) values, particularly from the start of the protocol until the anaerobic threshold (AT) was reached, demonstrating (e.g., together with the results shows in FIGS. 6 and 7) that the methods disclosed herein are suitable for continuous or semi-continuous monitoring of subjects. Values for both whole body $\dot{V}O_2$ and $\dot{V}O_2$ (abs) for all ten test subjects from the start of the protocol until the anaerobic threshold was reached for each subject are shown in FIG. 18. The values are well correlated, with $R^2=0.89$ and an average difference of 0.06 L/min. between whole body $\dot{V}O_2$ and $\dot{V}O_2$ (abs).

Above the anaerobic threshold, differences between whole body $\dot{V}O_2$ and $\dot{V}O_2$ (abs) may be attributable to differences between muscle oxygen saturation (measured by the performance monitors disclosed herein) and actual venous oxygen saturation. For example, above the anaerobic threshold, myoglobin desaturation may represent a significant contribution to measured muscle oxygen saturation. Differences in this example may also be a result of an inaccurate estimation of stroke volume at high work loads.

As discussed above, the relative oxygen consumption rates, $\dot{V}O_2$ (NIRS), that are determined according to Equations (1) and (2) correspond to $\dot{V}O_2$ normalized by the stroke volume (SV), which corresponds to the volume of blood a subject's heart pumps with each beat. If SV is known for a particular subject during exercise, then the relative measurement of the subject's oxygen consumption rate can be converted into an absolute measurement of oxygen consumption rate. In some embodiments, for example, SV can be measured through echocardiography or via bioimpedance measurements. Alternatively, or in addition, SV can be estimated from correlation tables or other such reference data that relate SV to one or more other parameters that are measured by the performance monitors disclosed herein, or SV can be measured via an external device that interfaces with the performance monitors. SV can be dependent upon a subject's gender, level of fitness, and/or other attributes, and the correlations between SV and the one or more other parameters can take account of the manner in which SV can vary according to subject.

Further, as discussed above, in some embodiments, SV can be calculated based on one or more measured parameters such as HR. If HR (or the other parameters which are used to determine SV) are determined in real-time, SV can also be determined in real-time. An equation such as Equation (5) can be used to calculate SV values from measured HR data. In general, a variety of different mathematical equations can be used to determine SV from measured values of parameters such as HR.

Figure 8:
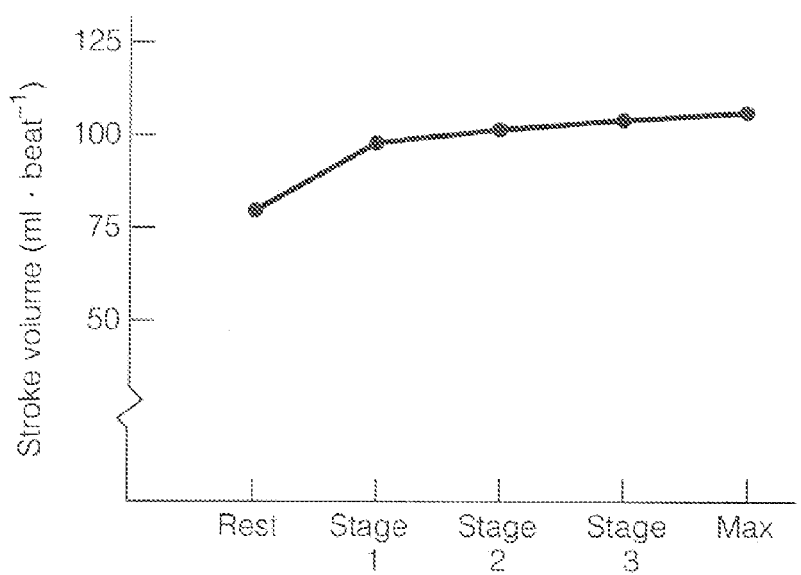
FIG. 8 is a plot of stroke volume as a function of exercise intensity.

A measurement of SV can be recorded each time $\dot{V}O_2$ (NIRS) is determined for the test subject. Further, in certain embodiments, it may even be sufficient to determine SV less frequently than the frequency with which $\dot{V}O_2$ (NIRS) is measured, as SV may not change significantly during periods of physical exertion. For example, as shown in FIG. 8, SV does not always vary significantly over the course of a particular physical activity; in this example, it would not typically be necessary to continuously determine SV for the subject to obtain accurate estimates of the absolute oxygen consumption rate in the subject. Instead, measurements of SV taken at one or a small number of time points can be used during continuous monitoring of the subject over an extended time period.

Figure 9:
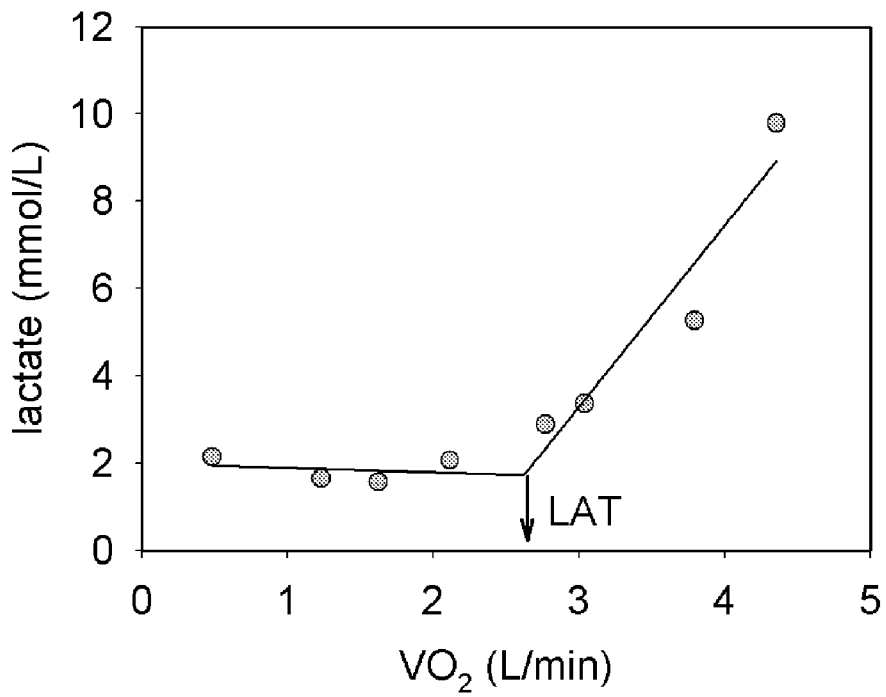
FIG. 9 is a plot of lactate concentration showing an anaerobic threshold for a test subject.

Lactate concentration values were plotted against values of $\dot{V}O_2$ determined from metabolic cart measurements in the graph shown in FIG. 9. To determine the anaerobic threshold, lactate concentration values were analyzed with a simultaneous bilinear regression using the fitting equation given by Equation (6):

$$y = \begin{cases} y_1 + s_1(x - x_0), & x < x_0 \\ y_2 + s_2(x - x_0), & x > x_0 \end{cases} \quad (6)$$

where y is a value of lactate concentration, $s_1$ and $S_2$ are the slopes of the two linear segments of the bilinear fitting curve, $y_1$ and $y_2$ are intercepts of the two linear segments of the bilinear fitting curve, x corresponds to $\dot{V}O_2$, and $x_0$ is the value of $\dot{V}O_2$ where the first derivative of lactate concentration vs. $\dot{V}O_2$ changes. The value $x_0$, which is common to both segments in the bilinear fitting equation, corresponded to the anaerobic threshold, and is shown as "LAT" in FIG. 9.

Figure 10:
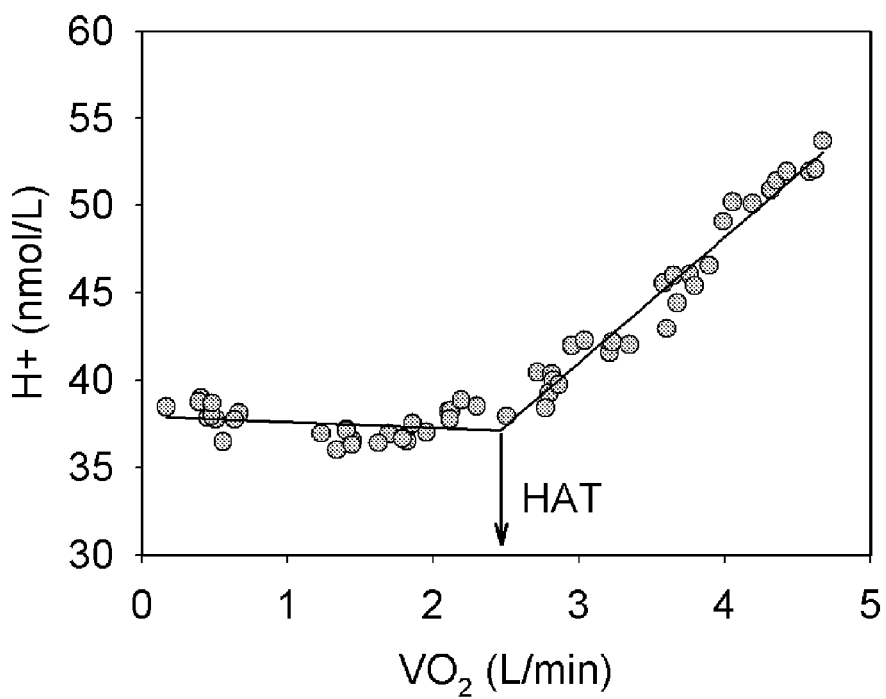
FIG. 10 is a plot of hydrogen ion concentration showing an anaerobic threshold for a test subject.

The anaerobic threshold can also be determined from measurements of [$H^+$] and/or from pH measurements recorded via the performance monitor. Because [$H^+$] and/or pH are/is related to the lactate concentration, the anaerobic threshold determined via [$H^+$] and/or pH measurements is correlated with the anaerobic threshold determined directly via blood lactate concentration measurements. Values of [$H^+$] are plotted against values of $\dot{V}O_2$ determined from metabolic cart measurements in the graph shown in FIG. 10. Anaerobic threshold ("HAT" in FIG. 10) was determined by fitting the data in FIG. 10 to Equation (6), where y corresponds to a value of [$H^+$]. As shown in FIG. 10, the anaerobic threshold is a value of $\dot{V}O_2$ that is common to both segments in the bilinear fitting equation, and corresponds to the oxygen consumption rate at which the first derivative of [$H^+$] vs. $\dot{V}O_2$ changes.

Figure 11:
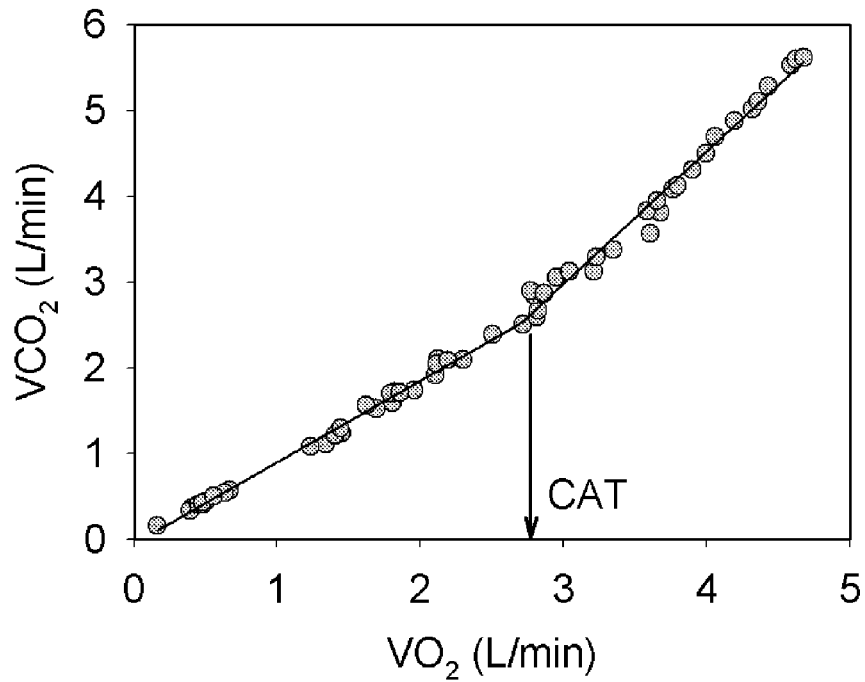
FIG. 11 is a plot of a rate of carbon dioxide production showing an anaerobic threshold for a test subject.

Further, the anaerobic threshold can be determined from measurements of carbon dioxide produced during the exercise protocol. Values of the rate of carbon dioxide production ($VCO_2$) are plotted against values of $\dot{V}O_2$ determined from metabolic cart measurements in the graph shown in FIG. 11. Anaerobic threshold ("CAT" in FIG. 11) was determined by fitting the data in FIG. 11 to Equation (6), where y corresponds to a value of $VCO_2$. As shown in FIG. 11, the anaerobic threshold is a value of $\dot{V}O_2$ that is common to both segments in the bilinear fitting equation, and corresponds to the oxygen consumption rate at which the first derivative of $VCO_2$ vs. $\dot{V}O_2$ changes.

Measured quantities such as lactate concentration, $VCO_2$, and [$H^+$] can be plotted against quantities other than $\dot{V}O_2$ to determine anaerobic threshold. In general, lactate concentration, $VCO_2$, and [$H^+$] can be plotted against any quantity which measures exercise intensity during a testing protocol, and Equation (6) or another mathematical algorithm can be used to determine anaerobic threshold from the measured data.

As observed by comparing the anaerobic thresholds determined in FIGS. 9-11, anaerobic thresholds determined via near-infrared measurements of [$H^+$] are correlated with anaerobic thresholds determined directly from blood lactate measurements and carbon dioxide production, even though the curve in FIG. 11 was not as strongly bilinear as the curves in FIGS. 9 and 10. The anaerobic threshold determined from blood lactate measurements was 1.95±0.27 L/min, the anaerobic threshold determined from $VCO_2$ measurements was 1.64±0.08 L/min, and the anaerobic threshold determined from [$H^+$] measurements was 1.64±0.15 L/min. The standard error for the blood lactate measurements was larger because fewer data points were available for each subject for anaerobic threshold determination.

Figure 12:
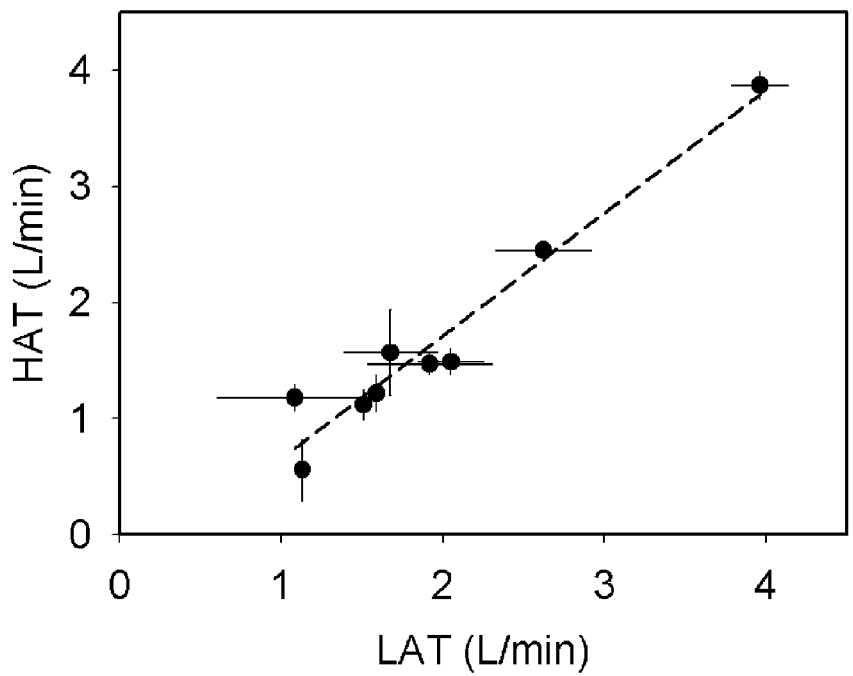
FIG. 12 is a plot showing anaerobic thresholds determined from lactate concentration and hydrogen ion concentration for nine test subjects.

The relationship between anaerobic threshold measured from blood lactate and [$H^+$] is shown in FIG. 12 for nine of the subjects under study. An average correlation coefficient of $R^2=0.946$ was obtained. A regression line (dotted) fitted to the data in FIG. 12 had a slope of 1.06. Typically, the value of anaerobic threshold determined from near-infrared measurements of [$H^+$] is lower than the value of anaerobic threshold measured directly. This is expected, because pH measurements made via near-infrared reflectance and/or absorbance spectroscopy assess interstitial fluid [$H^+$], which more closely tracks hydrogen ion transport out of cells than blood lactate measurements, which average lactate concentrations from several sources.

Figure 13:
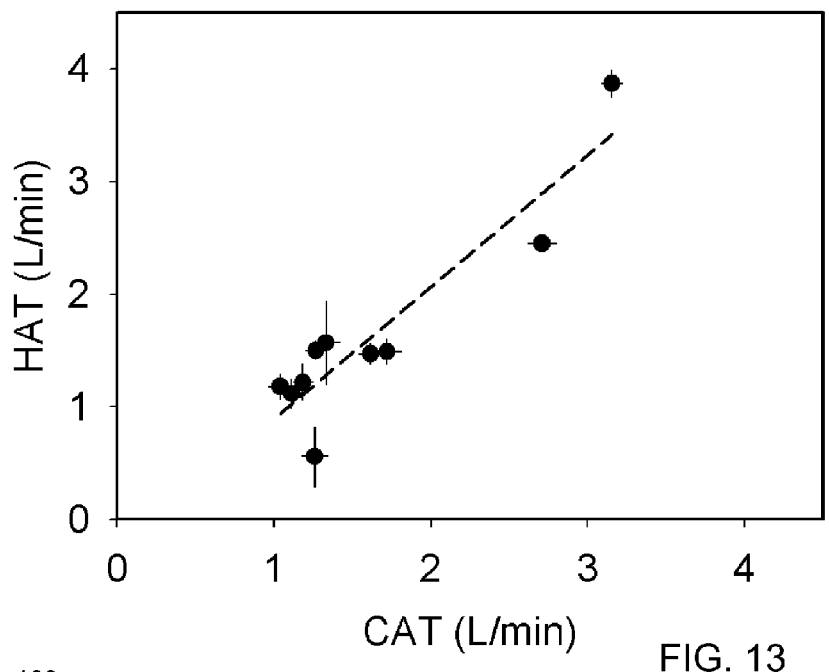
FIG. 13 is a plot showing anaerobic thresholds determined from hydrogen ion concentration and carbon dioxide production rate for ten test subjects.

The relationship between anaerobic threshold measured from carbon dioxide produced and [$H^+$] is shown in FIG. 13 for the ten subjects under study. An average correlation coefficient of $R^2=0.849$ was obtained. A regression line (dotted) fitted to the data in FIG. 13 had a slope of 1.17, indicating a strong positive correlation.

One advantage of determining anaerobic threshold via near-infrared spectroscopic measurements is that the measurements can be performed continuously (or nearly-continuously) and in real-time. Typically, in standard measurements of anaerobic threshold, a subject exercises to capacity and his/her anaerobic threshold is determined afterward based on lactate measurements from drawn blood. However, the monitors disclosed herein are capable of significantly faster (e.g., real-time or nearly real-time) measurement of anaerobic threshold and other parameters, in comparison with conventional devices.

In some embodiments, for example, the performance monitors disclosed herein can perform measurements and/or determine parameter values based on spectral data at a frequency of 0.01 Hz or more (e.g., 0.05 Hz or more, 0.1 Hz or more, 0.5 Hz or more, 1 Hz or more) and/or 30 Hz or less (e.g., 20 Hz or less, 10 Hz or less, 6 Hz or less, 4 Hz or less, 2 Hz or less).

The requirement of exercise to maximum capacity increases the risk of a cardiac event in the subject. However, by determining anaerobic threshold via the performance monitors disclosed herein, trends in hydrogen ion concentration as a function of exercise intensity can be continually followed by monitoring changes in slope of the hydrogen ion concentration curve. As a result, the subject only exercises at a level slightly above the anaerobic threshold to complete the measurement; that is, there is no requirement for maximal exercise, reducing health risks for the subject and shortening the time required for assessment. Further, hydrogen ion concentration is determined through direct measurement of the subject's tissue, permitting the subject to exercise at a level that corresponds to the anaerobic threshold. For purposes of athletic training, an athlete can adjust his or her training regimen so that the athlete continues to train at or near the hydrogen ion concentration (e.g., measured using the monitors disclosed herein) that corresponds to his or her anaerobic threshold, which is known to be an effective training technique for endurance sports, for example.

Measurements of anaerobic threshold and oxygen consumption rates can be used together for assessment and monitoring of subjects in some embodiments. For example, oxygen consumption rates can be measured to follow exercise intensity of a subject undergoing an exercise protocol to determine anaerobic threshold. Anaerobic threshold can be determined from a change in slope of the hydrogen ion concentration as a function of oxygen consumption rate in the subject. Once a pH value and/or a hydrogen ion concentration value that corresponds to a subject's anaerobic threshold has been determined, the subject can be monitored during periods of physical exercise by measuring the subject's pH and/or hydrogen ion concentration (e.g., using the monitors disclosed herein). By maintaining an exercise intensity that results in the subject remaining at or near his/her anaerobic threshold, the effectiveness of the exercise can be determined. Typically, for example, athletic training regimens that keep a subject at or near his/her anaerobic threshold during training are effective at increasing endurance and improving other performance criteria.

Alternatively, or in addition, the subject's pH and/or hydrogen ion can be monitored before and/or after one or more periods of physical exercise to determine an extent of physical exertion of the subject during the exercise. If the subject's level of physical exertion is considerable, the monitored values of pH and/or hydrogen ion concentration before and after exercise may differ significantly, indicating that the subject is closer (e.g., significantly closer) to his/her anaerobic threshold following the exercise. If the level of exertion is relatively minor, then only small changes in pH and/or hydrogen ion concentration may be observed, indicating that the subject is not near his/her anaerobic threshold.

Other Embodiments

It is to be understood that the foregoing description is intended to illustrate and not limit the scope of the disclosure, which is defined by the scope of the appended claims. Other aspects, advantages, and modifications are within the scope of the following claims.

What is claimed is:

1. An apparatus, comprising:
    a spectrometer configured to detect light emitted from a tissue of a human or animal subject, and to determine a spectrum of the tissue from the detected light; and
    an electronic processor coupled to the spectrometer and configured to:
        determine a plurality of spectra of the tissue;
        determine a plurality of pH values of the tissue, wherein each one of the plurality of pH values is obtained from a different one of the plurality of spectra; and
        determine an anaerobic threshold of the subject based on the plurality of pH values of the tissue and on corresponding values of a measure of exercise intensity.

2. The apparatus of claim 1, wherein the spectrometer comprises:
    at least one light source;
    one or more incident light ports configured to transmit light from the at least one light source to the tissue; and
    one or more light receiving ports configured to transmit light from the tissue to a detector,
    wherein the one or more incident light ports and the one or more light receiving ports are enclosed in a housing that comprises an attachment mechanism for attaching the housing to a portion of a subject's body.

3. The apparatus of claim 2, wherein the at least one light source comprises a plurality of light emitting diodes.

4. The apparatus of claim 2, wherein:
    the one or more light receiving ports comprise one light receiving port;
    the one or more incident light ports comprise a first light port positioned at a first distance from the light receiving port and a second light port positioned at a second distance, shorter than the first distance, from the light receiving port; and
    the electronic processor is configured to correct spectral data derived from light from the first light port with spectral data derived from light from the second light port.

5. The apparatus of claim 1, further comprising a communication interface in electrical communication with the electronic processor, the communication interface being configured to transmit signals from the electronic processor to a device over at least one of a communication link and a network.

6. The apparatus of claim 5, wherein the device is at least one of a computer, a handheld computing device, a mobile telephone, and a display device.

7. The apparatus of claim 5, wherein the signals comprise information about the subject, and the device is a computing device configured to monitor the information about the subject.

8. A system, comprising:
    an electronic device connected to a data transmission network; and
    a plurality of monitoring devices, each monitoring device corresponding to the apparatus of claim 1,
    wherein each monitoring device is configured to transmit information about one of multiple human or animal subjects to the electronic device over the data transmission network, the information comprising at least one of the oxygen consumption rate and the anaerobic threshold of the subject.

9. The apparatus of claim 1, wherein the measure of exercise intensity comprises an oxygen consumption rate.

* * * * *